United States Patent [19]

Sprecker et al.

[11] Patent Number: 4,492,645
[45] Date of Patent: Jan. 8, 1985

[54] ORGANOLEPTIC USE OF CYCLOHEXENYL-ALPHA-ALKYL ACROLEIN DERIVATIVES

[75] Inventors: Mark A. Sprecker, Sea Bright, N.J.; Philip T. Klemarczyk, Newington, Conn.; Robert P. Belko, Woodbridge, N.J.

[73] Assignee: International Flavors & Fragrances Inc., New York, N.Y.

[21] Appl. No.: 505,423

[22] Filed: Jun. 16, 1983

Related U.S. Application Data

[62] Division of Ser. No. 398,953, Jul. 16, 1982, Pat. No. 4,424,379.

[51] Int. Cl.³ .............................. C11B 9/00
[52] U.S. Cl. .................... 252/522 R; 252/522 A
[58] Field of Search .................. 252/522 R, 552 A

[56] References Cited

U.S. PATENT DOCUMENTS 4,416,902 11/1983 Mookherjee et al. .......... 252/522 R

Primary Examiner—Anton H. Sutto
Attorney, Agent, or Firm—Arthur L. Liberman

[57] ABSTRACT

Described are cyclohexenyl-alpha-alkyl acrolein derivatives defined according to the generic structure:

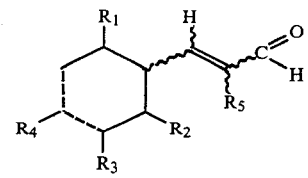

wherein $R_1$, $R_2$, $R_3$ and $R_4$ represent hydrogen or methyl with the proviso that one, two or three of $R_1$, $R_2$, $R_3$ and $R_4$ represent methyl; wherein $R_5$ represents methyl or ethyl; wherein one of the dashed lines represents a carbon-carbon double bond and the other of the dashed lines represents a carbon-carbon single bond; wherein the wavy lines represent the "cis" or "trans" juxtaposition of the moieties hydrogen, $R_5$, cyclohexenyl and carboxaldehyde about the carbon-carbon double bond; or represented by the structures:

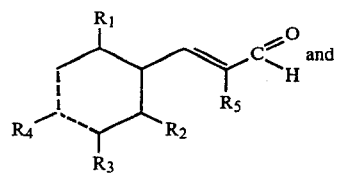

and

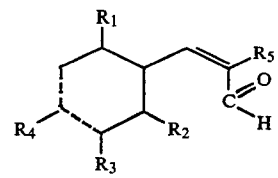

and processes and compositions for augmenting or enhancing the flavor and/or aroma of consumable materials including foodstuffs, chewing gums, medicinal products, toothpastes, chewing tobaccos, perfumes, perfumed articles, colognes, smoking tobaccos and smoking tobacco articles using as the essential ingredient at least one of said cyclohexenyl-alpha-alkyl acrolein derivatives.

15 Claims, 15 Drawing Figures

GLC PROFILE FOR EXAMPLE IB.

GLC PROFILE FOR EXAMPLE IA.

NMR SPECTRUM FOR PEAK 21 OF FIG. 2 FOR EXAMPLE IB.

IR SPECTRUM FOR PEAK 21 OF FIG.2 FOR EXAMPLE IB.

GLC PROFILE FOR EXAMPLE II.

NMR SPECTRUM FOR FRACTION 12 OF EXAMPLE II.

IR SPECTRUM FOR FRACTION 12 OF EXAMPLE II.

FIG. 9 NMR SPECTRUM FOR EXAMPLE III.

IR SPECTRUM FOR EXAMPLE III.

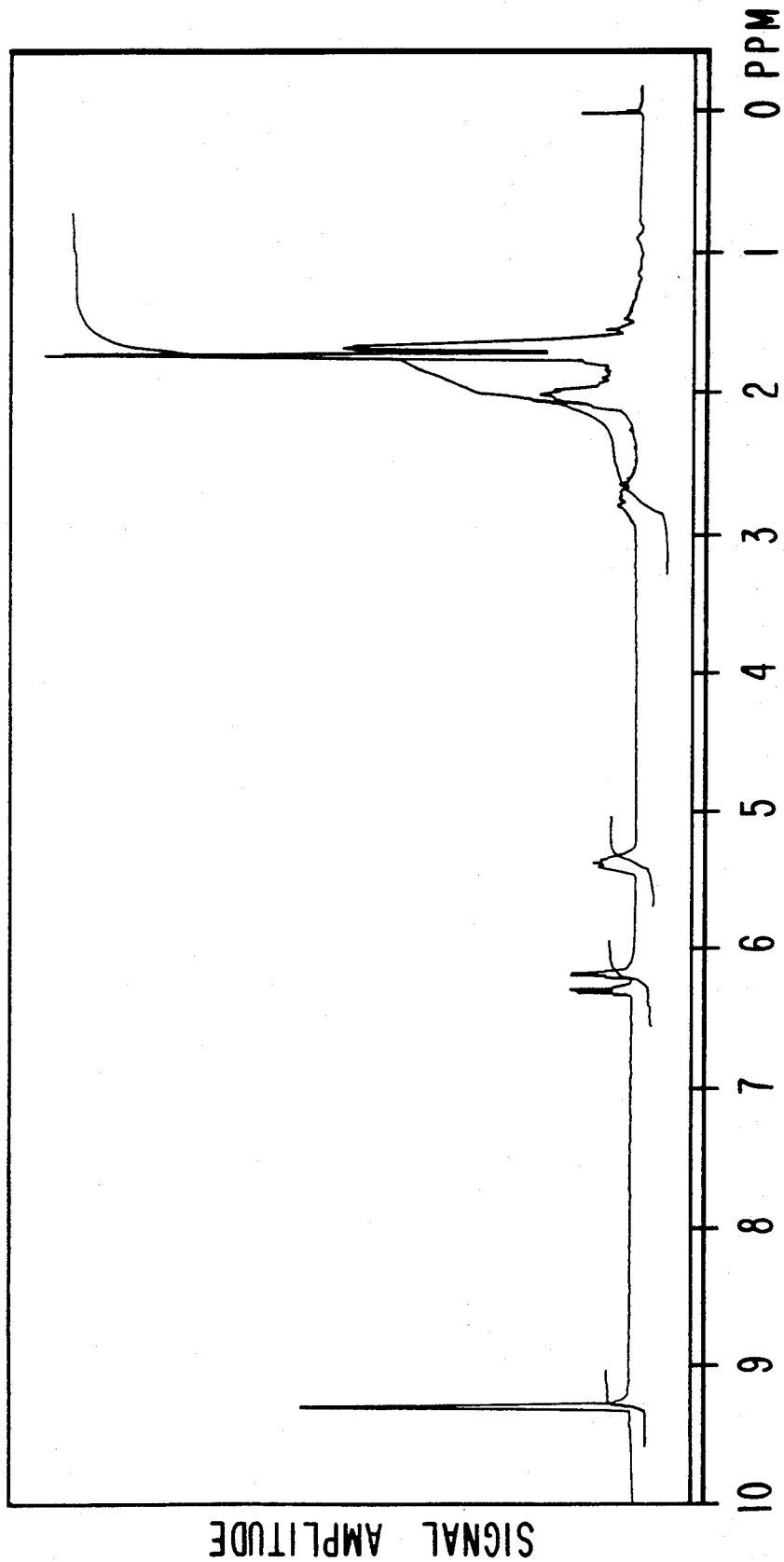
FIG.12 NMR SPECTRUM FOR FRACTION 7 OF EXAMPLE IV.

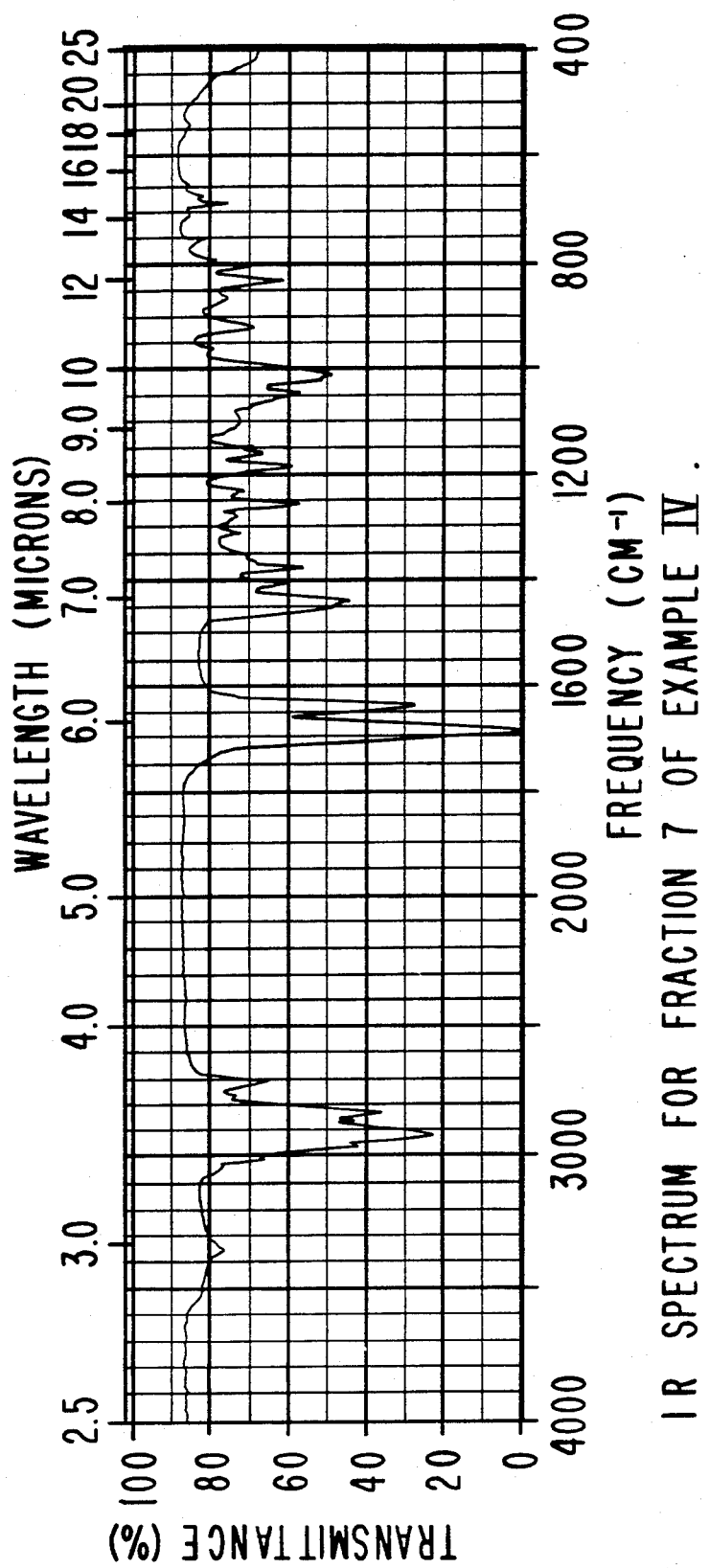

ORGANOLEPTIC USE OF CYCLOHEXENYL-ALPHA-ALKYL ACROLEIN DERIVATIVES

This is a divisional of application Ser. No. 398,953, filed July 16, 1982, now U.S. Pat. No. 4,424,379.

BACKGROUND OF THE INVENTION

The instant invention provides the cyclohexenyl-alpha-alkyl acrolein derivatives defined according to the generic structure:

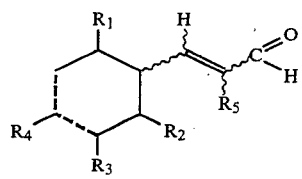

wherein $R_1$, $R_2$, $R_3$ and $R_4$ represent hydrogen or methyl with the proviso that one, two or three of $R_1$, $R_2$, $R_3$ and $R_4$ represent methyl; wherein $R_5$ represents methyl or ethyl; wherein one of the dashed lines represents a carbon-carbon double bond and the other of the dashed lines represents a carbon-carbon single bond; wherein the wavy lines represent the "cis" or "trans" juxtaposition of the moieties hydrogen, $R_5$, cyclohexenyl and carboxaldehyde about the carbon-carbon double bond; and uses thereof for their organoleptic properties in consumable materials.

Materials which provide powerful, green, cumin-like, spicy, cinnamon-like, natural orris, floral (violet-like), animalic, musky, floral (lily/lilac), ionone-like, orris-like, burnt orris, pungent fresh green, woody and "tropical rain forest" aromas are highly desirable in the art of perfumery. Many of the natural materials which provide such fragrances and contribute such desired nuances to perfumery compositions are high in cost, vary in quality from one batch to another and/or are generally subject to the usual variations of natural products.

By the same token, materials which can provide powerful, spicy, cinnamon, cumin-like, green and dandelion leaf-like aroma and taste nuances are highly desirable in the art of flavorings for foodstuffs, toothpastes, chewing gums, chewing tobaccos and medicinal products. Many of the natural materials which provide such flavor notes and contribute such desired nuances to flavoring compositions are high in costs, vary in quality from one batch to another and/or are generally subject to the usual variations of natural products.

Hay-clover-like, sweet, rich-tobacco, floral, fruity, green and earthy aroma and taste nuances are highly desirable for many uses in flavoring smoking tobacco compositions and smoking tobacco article components.

Arctander "Perfume and Flavor Chemicals (Aroma Chemicals)", Volume II, at monograph 2896, discloses that tetrahydro cinnamic aldehyde having the structure:

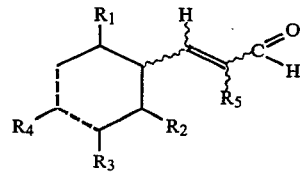

has a powerful, sweet-green, leafy, delicately creamy odor. Arctander further discloses:

"The title aldehyde, commonly referred to under the title name, was developed many years ago in continuation of the search for interesting aldehydes from the Claisen reaction, by which Cinnamic aldehyde had been produced. It was also based upon a new method of obtaining Cyclohexene aldehydes and homologues of same.

The subject material has found some application in perfumery, and so has the Cyclohexene carboxaldehyde from which it is made. The parent cyclic aldehyde has a powerful green-leafy odor, and it was interesting to see what type odor could be obtained by the Claisen condensation.

Although rarely offered under its proper chemical name, this material is still used in various perfume specialties and bases for its refreshing, green note, sometimes useful in Citrus compositions, but also used in Chypres, Fougeres, etc. in combination with Oakmoss, Lavender, etc.

It is produced from Acrolein and Butadiene to make Cyclohex-3-enealdehyde. By condensation (Claisen) with Acetaldehyde the title material is obtained."

Arctander, at monograph 2896, refers to French Pat. No. 672025 published on Dec. 21, 1929. In said French Pat. No. 672025, the Diels-Alder reactions of acrolein derivatives with conjugated dienes to produce cyclohexene carboxaldehydes are disclosed. Thus, for example, the reaction:

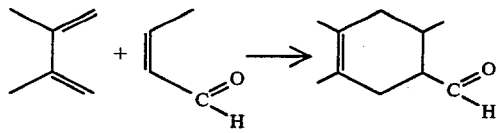

is disclosed to produce a perfumery compound. Furthermore, French Pat. No. 672025 discloses that the resulting carboxaldehydes can be further reacted with ketones to produce irone-type derivatives at page 3, lines 75-82 and at page 4, lines 1-5.

Neither the French Pat. No. 672025 nor the Arctander reference discloses or infers that the compounds defined according to the structure:

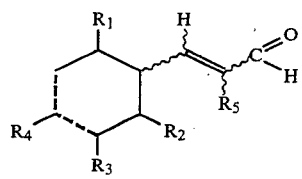

has desirable organoleptic properties which are unexpected, unobvious and advantageous.

Arctander "Perfume and Flavor Chemicals (Aroma Chemicals)", Volume I, at monograph 761 discloses the use of iso-Cyclocitral which is a mixture of compounds having the structures:

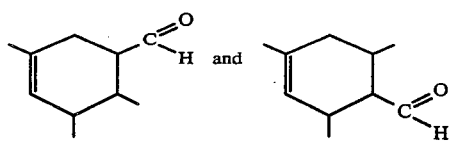

for its organoleptic properties thusly:

"Powerful, and diffusive, foilage-green, "dark"-weedy and dry odor, sometimes described as "Flower-shop odor". The earthy and wet-green notes are quite natural in high dilution and resemble the odor of stems from plants and flowers fresh from the soil.

Finds use in perfume compositions where it blends excellently with Oakmoss products (compensates for sweetness and lifts the topnote), with Ionones (freshness), Geranium and Galbanum (enhances the green and "vegetable" notes), etc.

On account of its modest cost it also finds its way into masking odors for industrial purposes. Its power compensates for its cost (usually slightly less than Citral) for such purposes.

Produced by a Diels-Alder type condensation of 2-Methyl-2,4-pentadiene and Crotonaldehyde. The reaction product is a mixture of isomers commercially called iso-Cyclocitral (after rectification)".

At monographs 762 and 763, Arctander describes alpha-Cyclocitrylidene Acetaldehyde and beta-Cyclocitrylidene Acetaldehyde having the structures, respectively:

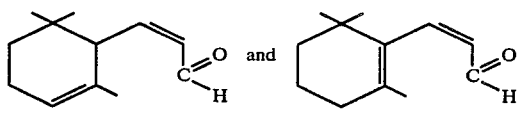

thusly:

762: alpha-Cyclocitrylidene Acetaldehyde

"Mild floral-woody, somewhat oily-herbaceous odor, remotely reminiscent of Rose with similarity to the odor of hydrogenated Ionones.

Suggested for use in perfume compositions. It brings a certain amount of floral lift to Rose compositions, and performs fairly well even in soap. However, the cost of the rarely offered and never readily available lots are rather discouraging to the perfumer, and it is most conceivable that this material can be left out of the perfumer's library without any great loss.

Produced from alpha-Cyclocitral and Acetaldehyde by condensation."

763: beta-Cyclocitrylidene Acetaldehyde

"Sweet-woody, rather heavy odor, resembling that of beta-Ionone. More fruity than really floral, but not as tenacious as the Ionone.

Suggested for use in perfume compositions, but since it does not offer any new or unusual odor characteristics, and it cannot be produced in economical competition to beta-Ionone, there is little or no chance that it will ever become a standard shelf ingredient for the perfumer.

Produced from beta-Cyclocitral and Acetaldehyde by condensation."

U.S. Pat. No. 3,031,507 discloses the use in perfumery of cyclohexylcrotonaldehyde having the structure:

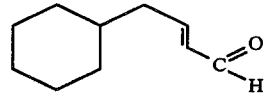

U.S. Pat. No. 3,313,843 discloses the use of cinnamaldehyde derivatives having the structure:

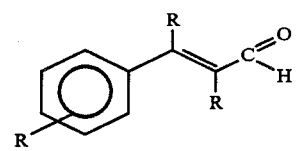

wherein R is hydrogen or methyl as intermediates for preparing other compounds.

Nothing in the prior art, above cited, or any other prior art infers or discloses the compounds having the generic structure:

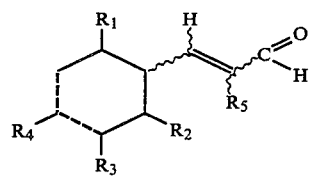

wherein $R_1$, $R_2$, $R_3$ and $R_4$ represent hydrogen or methyl with the proviso that one, two or three of $R_1$, $R_2$, $R_3$ and $R_4$ represent methyl; wherein $R_5$ represents methyl or ethyl; wherein one of the dashed lines represents a carbon-carbon double bond and the other of the dashed lines represents a carbon-carbon single bond; wherein the wavy lines represent the "cis" or "trans" juxtaposition of the moieties hydrogen, $R_5$, cyclohexenyl and carboxaldehyde about the carbon-carbon double bond.

Nothing in the prior art discloses that such compounds having the structure:

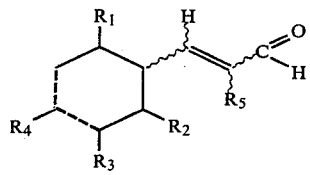

wherein $R_1$, $R_2$, $R_3$ and $R_4$ represent hydrogen or methyl with the proviso that one, two or three of $R_1$, $R_2$, $R_3$ and $R_4$ represent methyl; wherein $R_5$ represents methyl or ethyl; wherein one of the dashed lines represents a carbon-carbon double bond and the other of the dashed lines represents a carbon-carbon single bond; wherein the wavy lines represent the "cis" or "trans" juxtaposition of the moieties hydrogen, $R_5$, cyclohexenyl and carboxaldehyde about the carbon-carbon double bond; has such unexpected, unobvious and advantageous organoleptic properties.

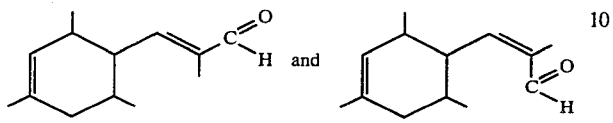

with a preponderance of the compound having the structure:

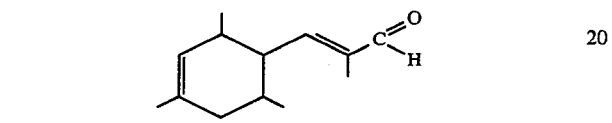

Figure 2:
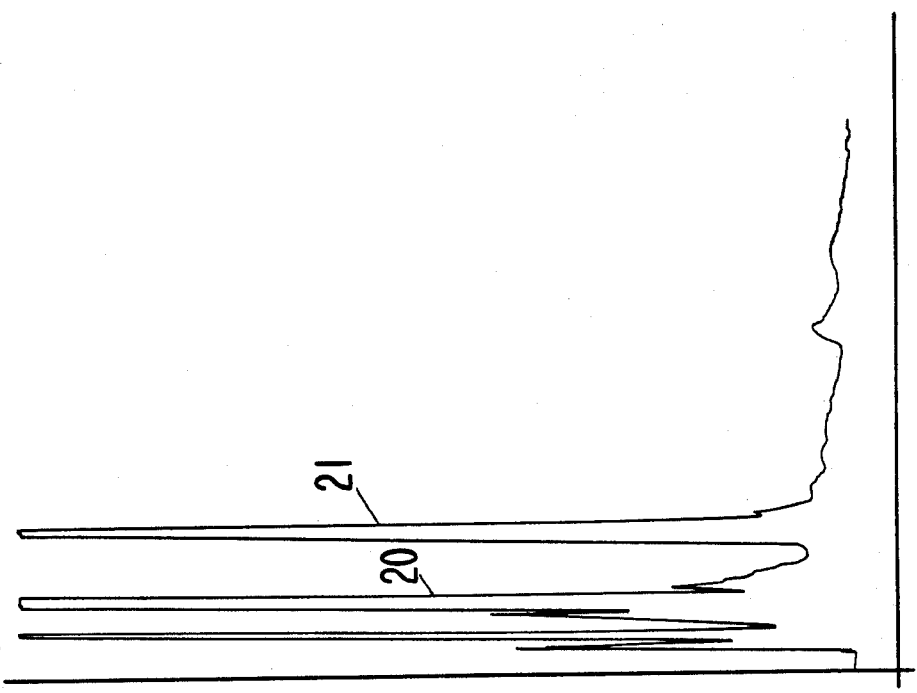

FIG. 2 is the GLC profile of the reaction product of Example I(B) containing the compounds having the structures:

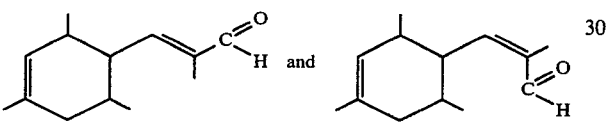

with a preponderance of the compound having the structure:

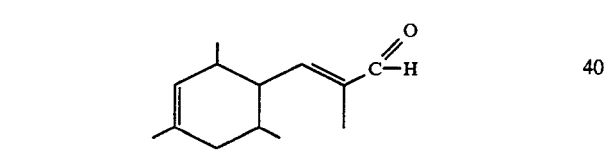

Figure 3:
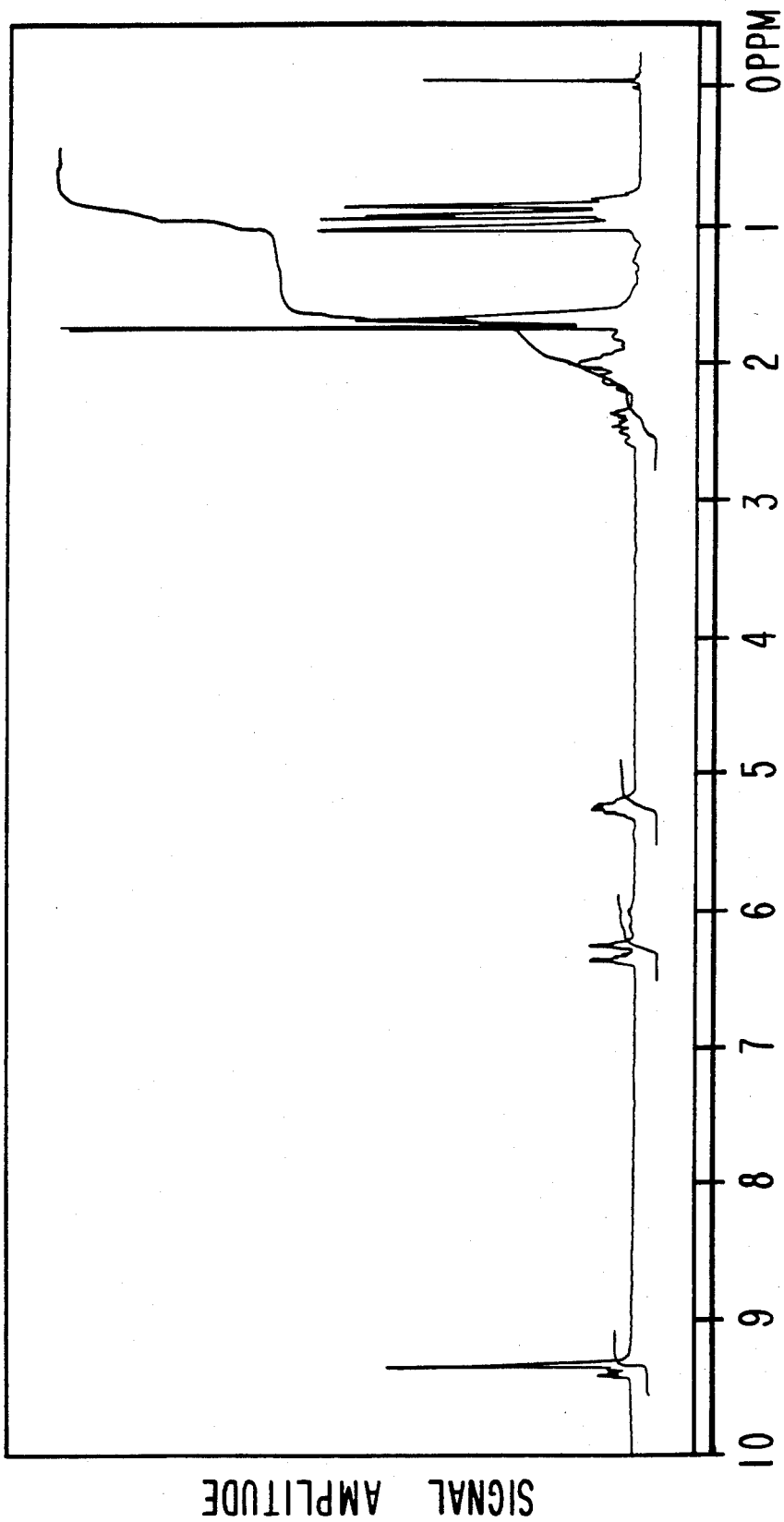

FIG. 3 is the NMR spectrum for the peak indicated by reference numeral "21" on the GLC profile of FIG. 2 which is for the compounds having the structures:

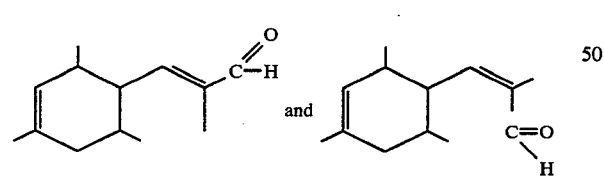

with a preponderance of the compound having the structure:

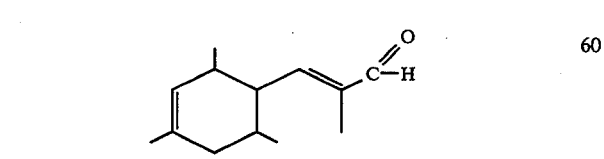

(solvent: CFCl₃; field strength 100 MH$_z$).

Figure 4:
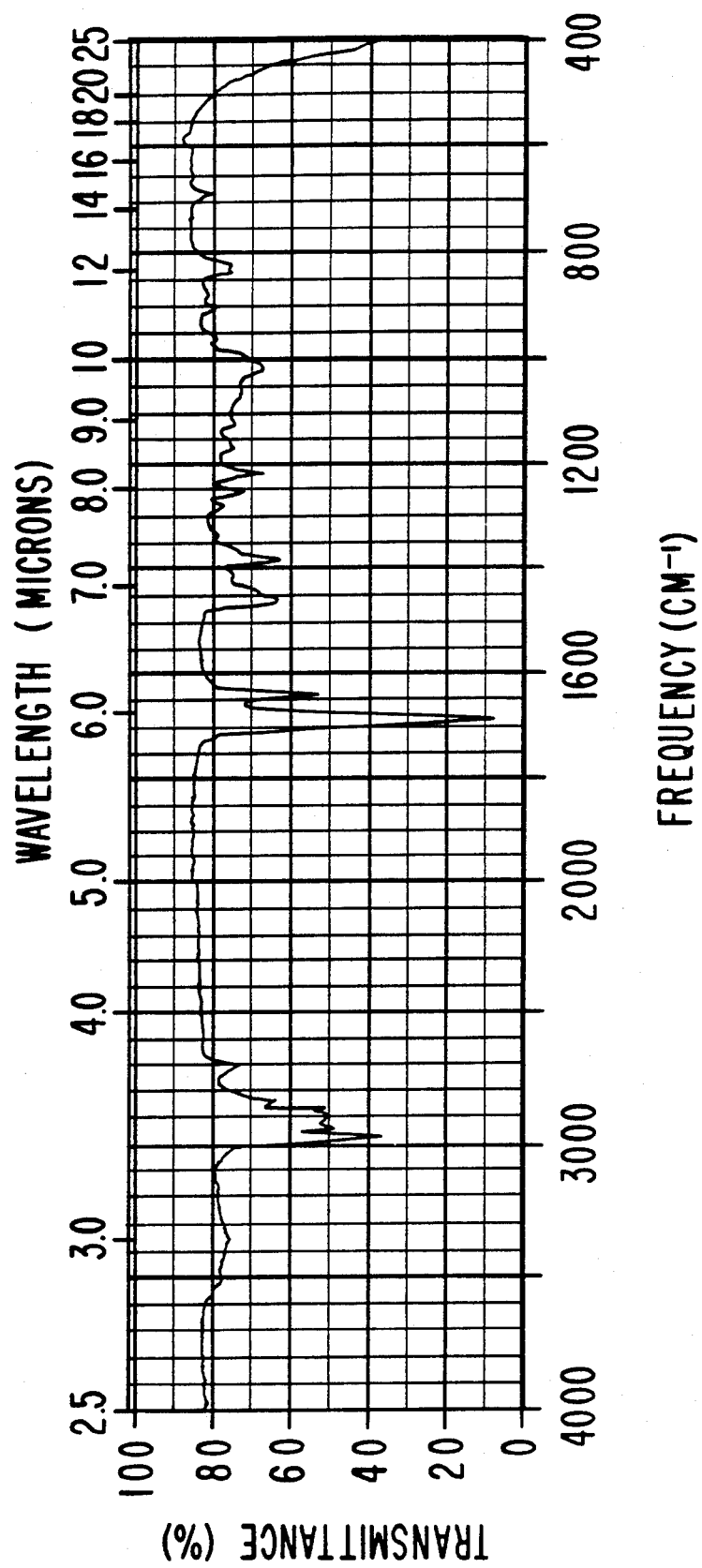

FIG. 4 is the infra-red spectrum for the compound of the peak indicated by reference numeral "21" on the GLC profile of FIG. 2 for the compounds having the structures:

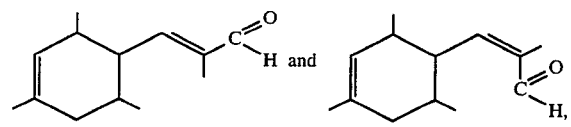

with a preponderance of the compound having the structure:

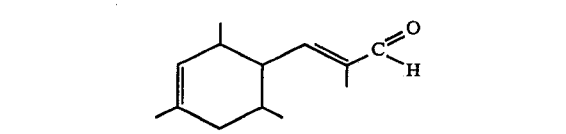

Figure 5:
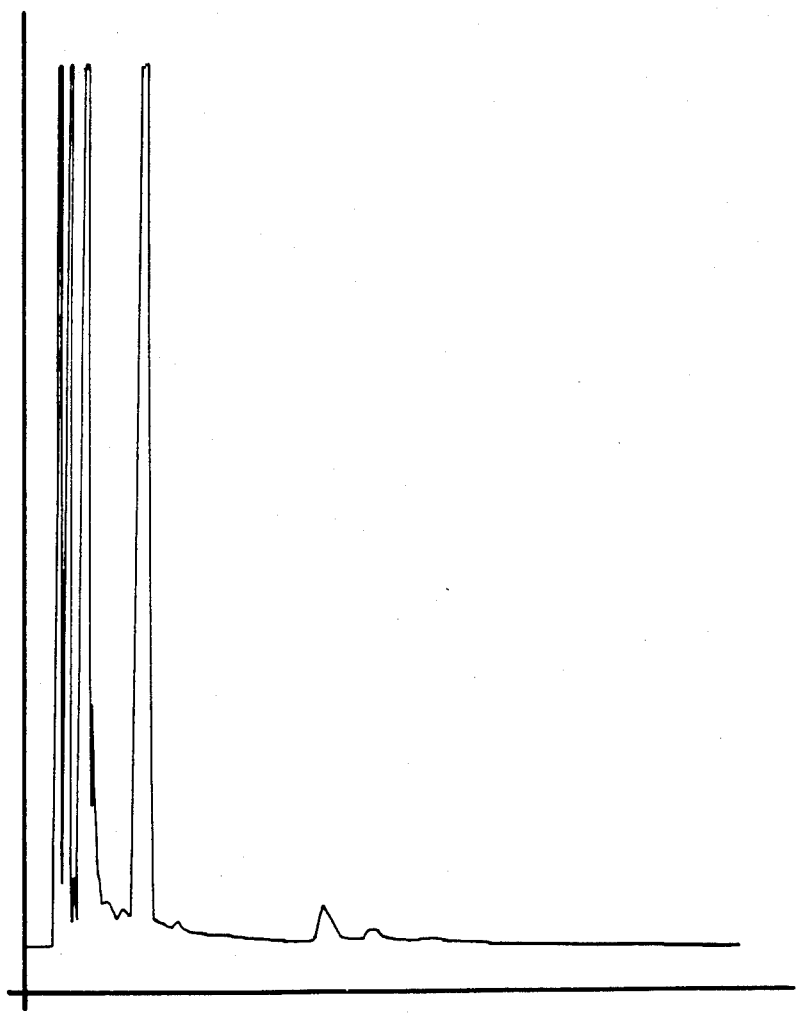

FIG. 5 is the GLC profile for the reaction product of Example II containing the compounds having the structures:

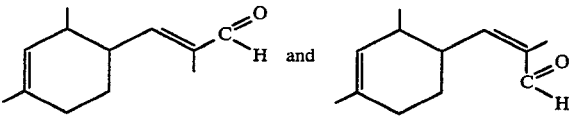

with a preponderance of the compound having the structure:

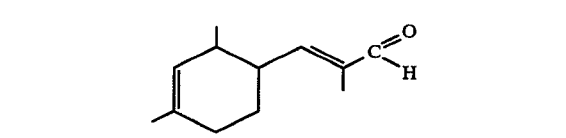

Figure 6:
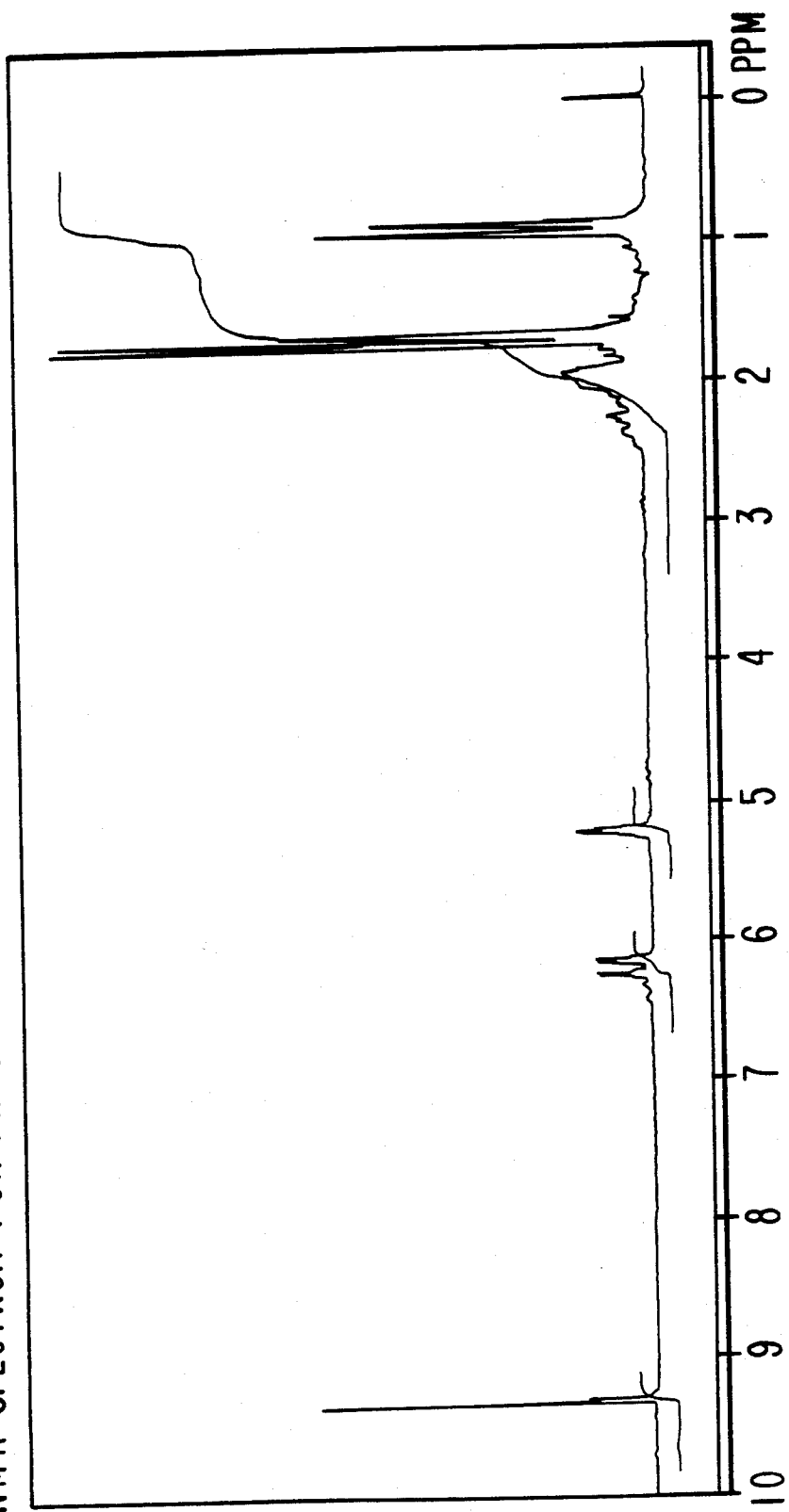

FIG. 6 is the NMR spectrum for Fraction 12 of the distillation product of the reaction product of Example II containing the compounds having the structures:

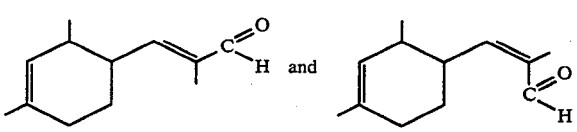

with a preponderance of the compound having the structure:

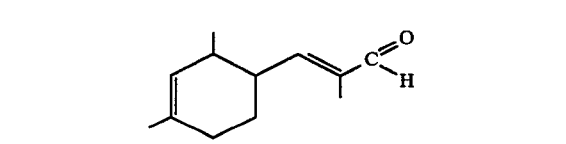

(solvent: CFCl₃; field strength 100 MH$_z$).

Figure 7:
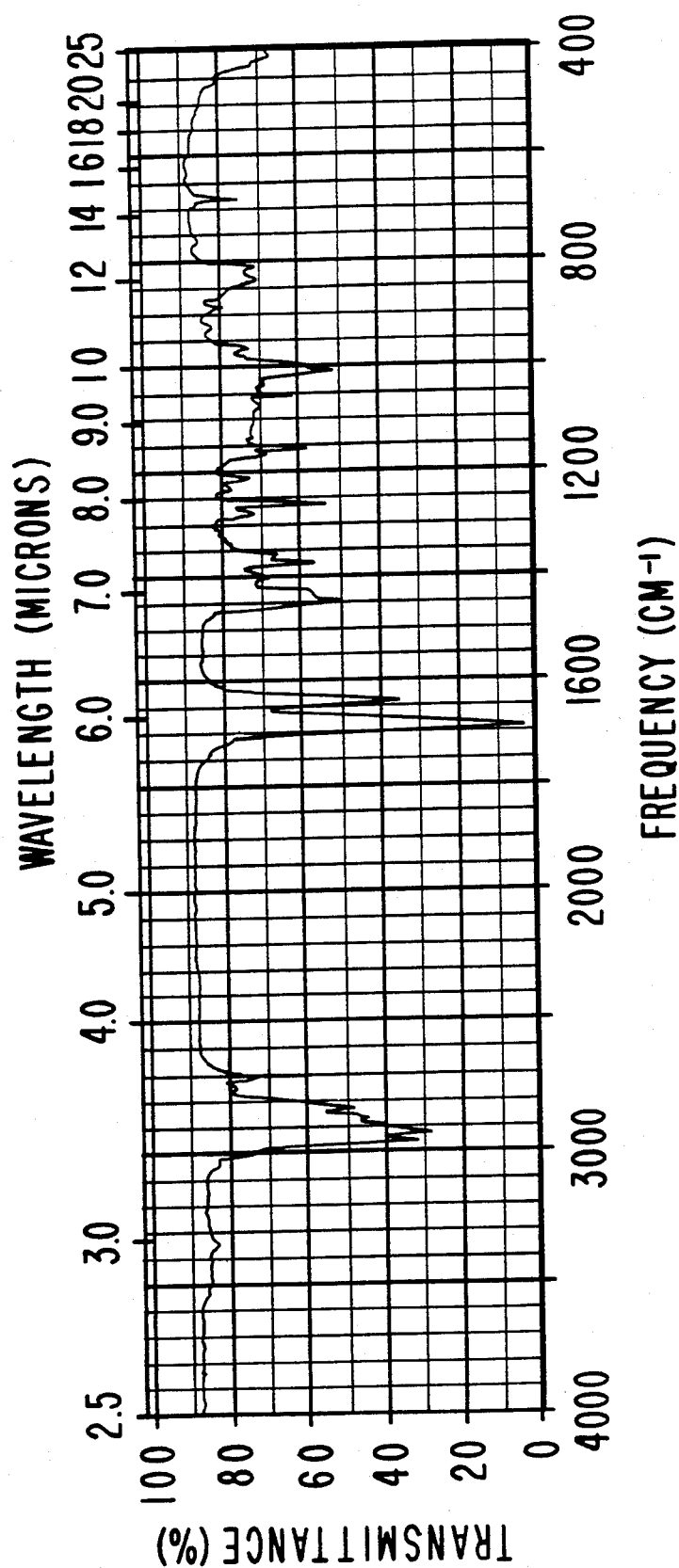

FIG. 7 is the infra-red spectrum for Fraction 12 of the distillation product of the reaction product of Example II containing the compounds having the structures:

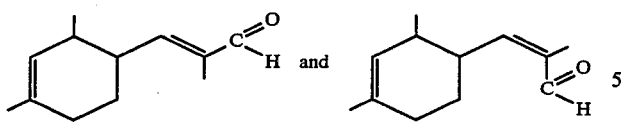 and with a preponderance of the compound having the structure:

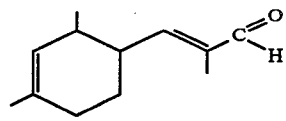

Figure 8:
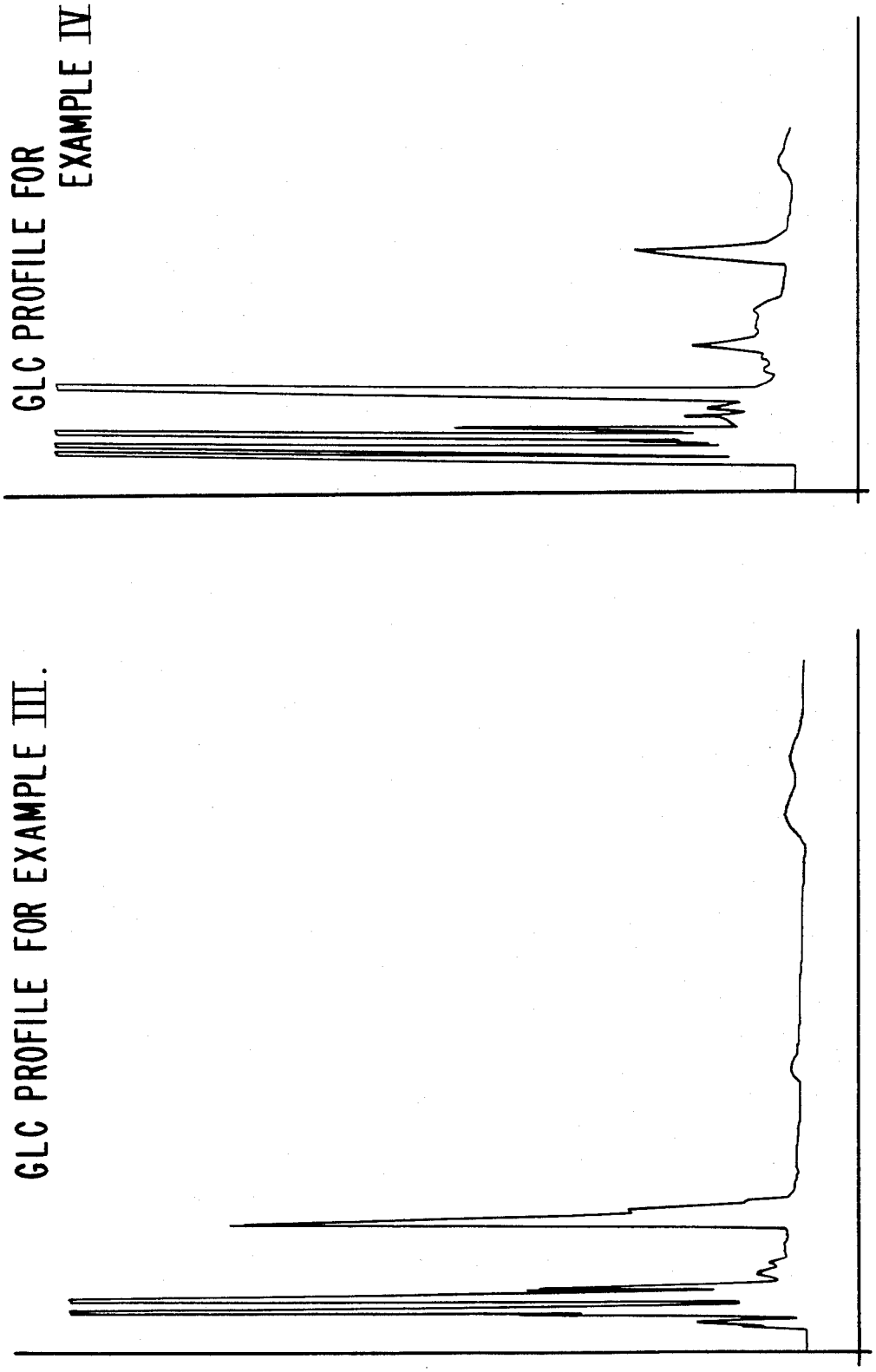

FIG. 8 is the GLC profile for the reaction product of Example III containing the compounds having the structures:

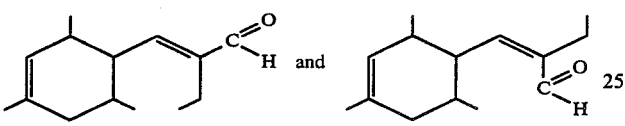 and with a preponderance of the compound having the structure:

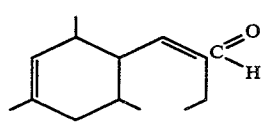

Figure 9:
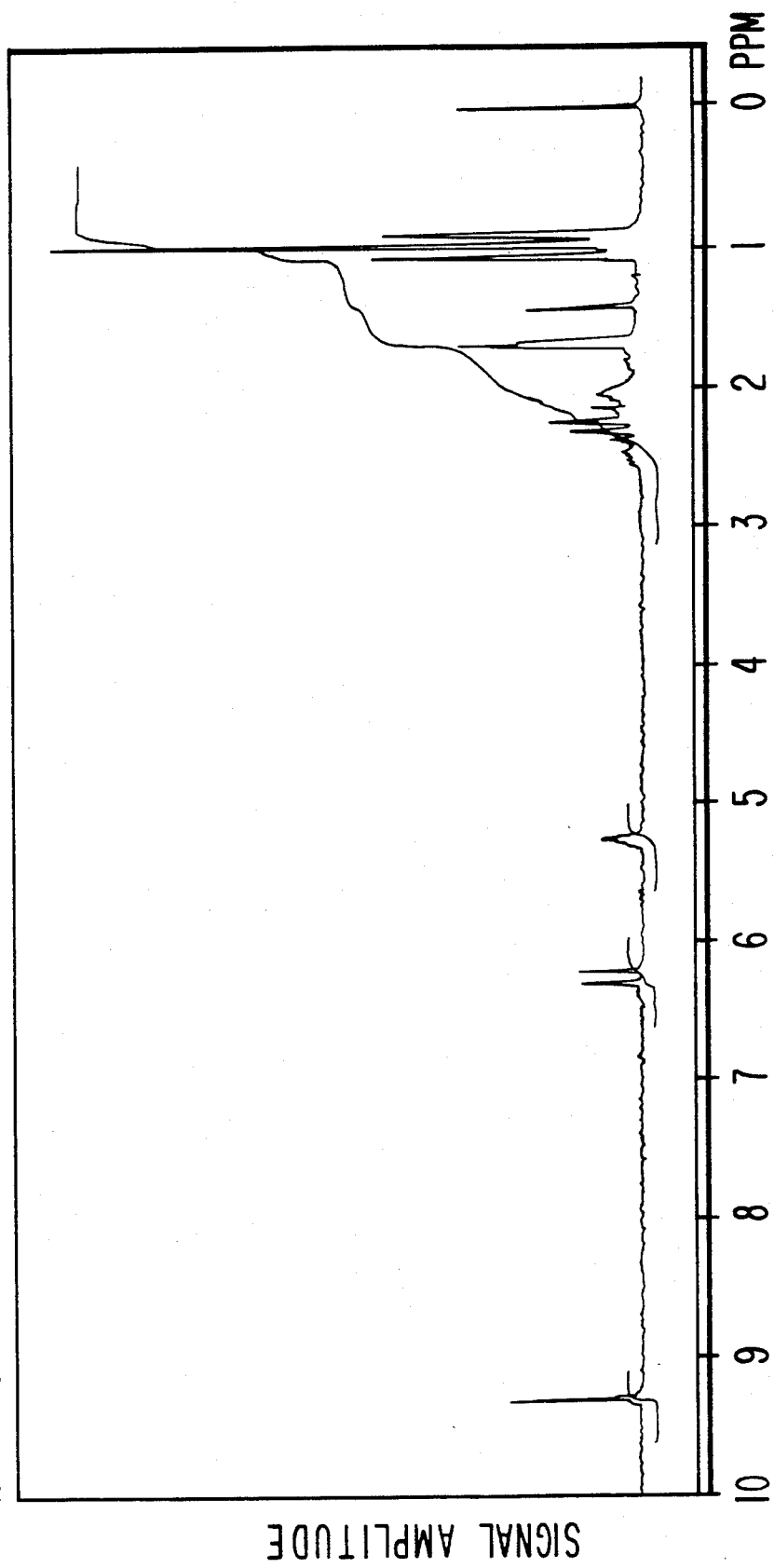

FIG. 9 is the NMR spectrum for the reaction product of Example III containing the compounds having the structures:

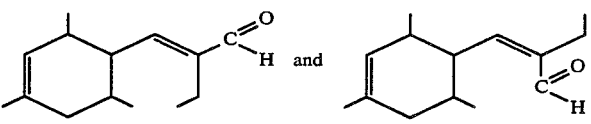 and with a preponderance of the compound having the structure:

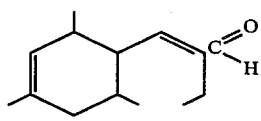

(solvent: CFCl₃; field strength 100 MH$_z$).

Figure 10:
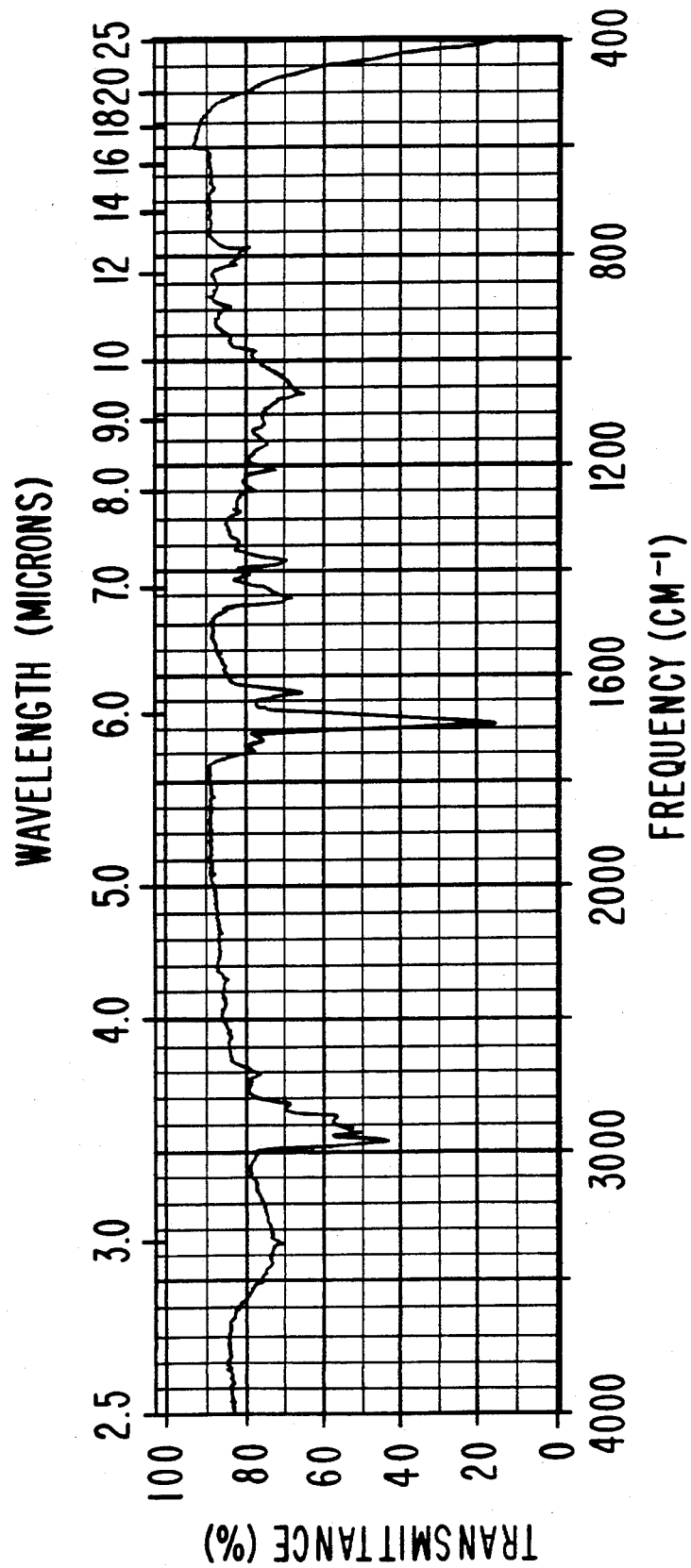

FIG. 10 is the infra-red spectrum for the reaction product of Example III containing the compounds having the structures:

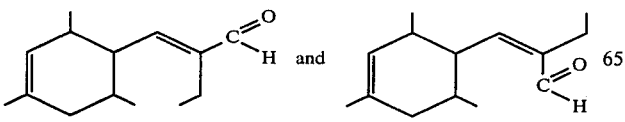 and with a preponderance of the compound having the structure:

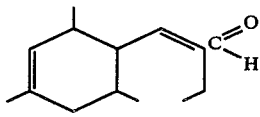

FIG. 11 is the GLC profile for the reaction product of Example IV containing the compounds having the structures:

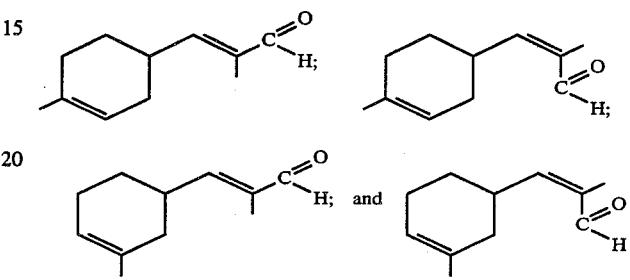

FIG. 12 is the NMR spectrum for Fraction 7 of the distillation product of the reaction product of Example IV containing the compounds having the structures:

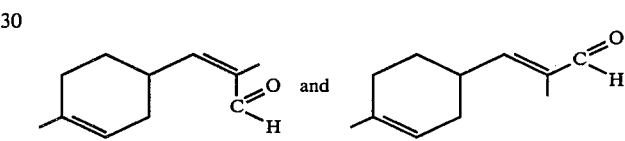 and with a preponderance of the compound having the structure:

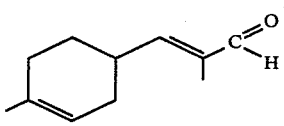

(solvent: CFCl₃; field strength 100 MH$_z$).

FIG. 13 is the infra-red spectrum for Fraction 7 of the distillation product of the reaction product of Example IV containing the compounds having the structures:

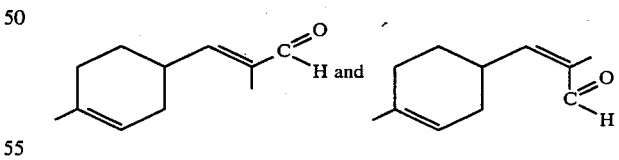 and with a preponderance of the compound having the structure:

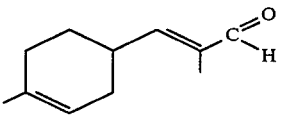

Figure 14:
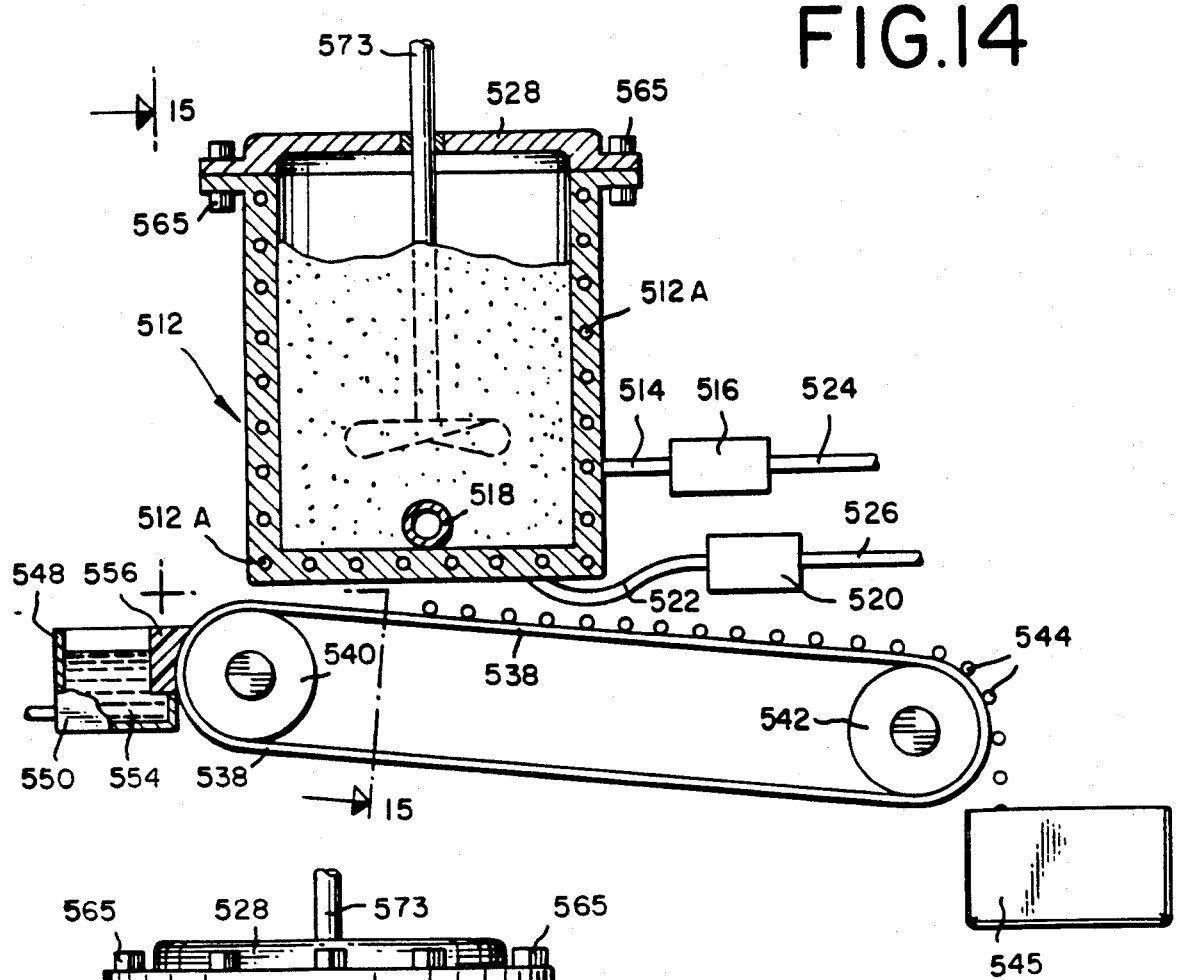

FIG. 14 is a cut-away side elevation view of the apparatus employed performing a perfumed article of our invention which perfumed article contains at least one of the substances defined according to the structure:

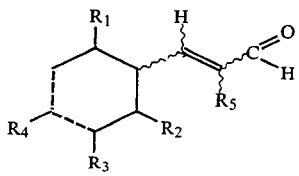

wherein $R_1$, $R_2$, $R_3$ and $R_4$ represent hydrogen or methyl with the proviso that one, two or three of $R_1$, $R_2$, $R_3$ and $R_4$ represent methyl; wherein $R_5$ represents methyl or ethyl; wherein one of the dashed lines represents a carbon-carbon double bond and the other of the dashed lines represents a carbon-carbon single bond; wherein the wavy lines represent the "cis" or "trans" juxtaposition of the moieties hydrogen, $R_5$, cyclohexenyl and carboxaldehyde about the carbon-carbon double bond.

Figure 15:
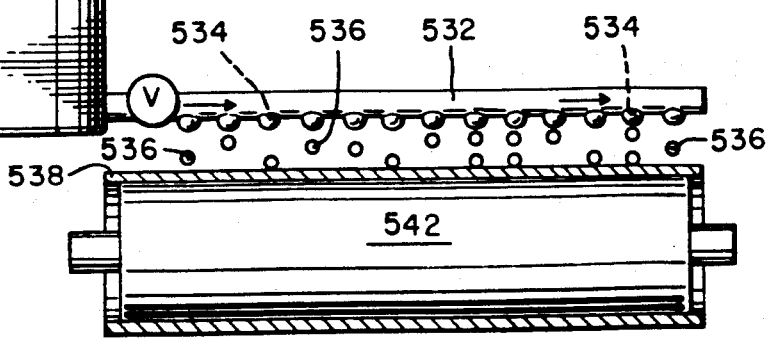

FIG. 15 is a cross-sectional view taken along lines 15—15 of FIG. 14.

DETAILED DESCRIPTION OF THE DRAWINGS

FIG. 2 is the GLC profile for the reaction product of Example I(B). The peak indicated by reference numeral "20" is the peak for the isocyclocitral reactant defined according to the structure:

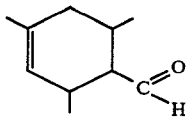

The peak indicated by reference numeral "21" is the peak for the reaction product containing the compounds defined according to the structures:

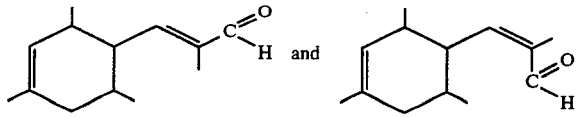

with a preponderance of the compound having the structure:

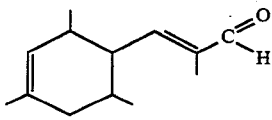

Referring to FIGS. 14 and 15, which show the apparatus for preparing scented polymers such as polyethylene, a quantity of thermoplastic polymer having a melting point of 220°–250° F. is placed in a container 512 as illustrated in FIGS. 14 and 15. 25 Pounds of a perfume formulation containing at least one of the cyclohexenyl-alpha-alkyl acrelein derivatives of our invention is then quickly added to the liquified molten polymer in container 512, the lid 528 is put in place and the agitating means 573 are actuated. The temperature is maintained at about 225° F. and the mixing is continued for about 5-15 minutes. The valve "V" is then opened to allow flow of the molten thermoplastic polymer (e.g., polyethylene) enriched with a scent-imparting substance containing at least one of the cyclohexenyl-alpha-alkyl acrolein derivatives of our invention, to exit through orifices 534. The liquid falling through orifices 534 solidifies almost instantaneously upon impact of the moving cooled conveyor 538. Thermoplastic polymer (e.g., polyethylene) beads or pellets 544 having a pronounced scent as described in the examples, infra resulting from the composition containing one of the cyclohexenyl-alpha-alkyl acrolein derivatives of our invention are thus formed. Analysis demonstrates that the pellets contain about 25% of a scent-imparting material containing one of the cyclohexenyl-alpha-alkyl acrolein derivatives of our invention so that almost no lost is in the scenting substance occur. The pellets are used as set forth, infra. The conveyor belt 538 is driven by rollers 540 and 542 with cooling apparatus 550 next to roller 540. The tank 512 is heated with heating elements 512A which are energized using an electric energy source evolved via wires 524/514 and 526/522. The solidified pellets are collected in container 546 for a subsequent utilization as set forth in the examples, infra.

THE INVENTION

This invention relates to novel cyclohexenyl-alpha-alkyl acrolein derivatives defined according to the structure:

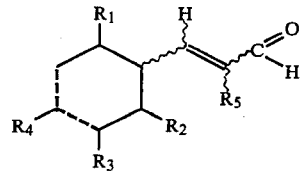

wherein $R_1$, $R_2$, $R_3$ and $R_4$ represent hydrogen or methyl with the proviso that one, two or three of $R_1$, $R_2$, $R_3$ and $R_4$ represent methyl; wherein $R_5$ represents methyl or ethyl; wherein one of the dashed lines represents a carbon-carbon double bond and the other of the dashed lines represents a carbon-carbon single bond; wherein the wavy lines represent the "cis" or "trans" juxtaposition of the moieties hydrogen, $R_5$, cyclohexenyl and carboxaldehyde about the carbon-carbon double bond; and uses thereof in augmenting or enhancing a variety of flavors and fragrances of various consumable materials.

Briefly, our invention also contemplates augmenting or enhancing the flavors and/or fragrances of such consumable materials as perfumes, perfumed articles (e.g., solid or liquid anionic, cationic, nonionic or zwitterionic detergents, fabric softeners, fabric softener articles, cosmetic powders, hair preparations such as shampoos and perfumed thermoplastic and thermo said resins), colognes, foodstuffs, chewing gums, toothpastes, medicinal products, chewing tobaccos, smoking tobaccos and smoking tobacco articles by adding thereto a small but effective amount of at least one cyclohexenyl-alpha-alkyl acrolein derivatives having the generic structure:

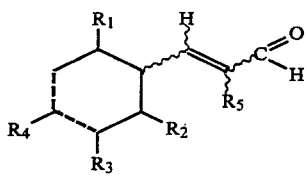

wherein $R_1$, $R_2$, $R_3$ and $R_4$ represent hydrogen or methyl with the proviso that one, two or three of $R_1$, $R_2$, $R_3$ and $R_4$ represent methyl; wherein $R_5$ represents methyl or ethyl; wherein one of the dashed lines represents a carbon-carbon double bond and the other of the dashed lines represents a carbon-carbon single bond; wherein the wavy lines represent the "cis" or "trans" juxtaposition of the moieties hydrogen, $R_5$, cyclohexenyl and carboxaldehyde about the carbon-carbon double bond.

The cyclohexenyl-alpha-alkyl acrolein derivatives of our invention augment, impart or enhance green, cumin-like, spicy, cinnamic, orris, floral (violet-like), animalic, musky, lily, lilac, ionone-like, burnt-orris, pungent, fresh green, woody, "tropical rain forest" aromas in or to perfumes, perfumed articles and colognes.

The cyclohexenyl-alpha-alkyl acrolein derivatives of our invention also augment, impart or enhance powerful spicy, cinnamon-like, cumin-like, green leafy and dandeloin leaf-like aroma and taste nuances of foodstuffs, chewing gums, toothpastes, medicinal products and chewing tobaccos.

The cyclohexenyl-alpha-alkyl acrolein derivatives of our invention also augment or enhance hay-clover-like, sweet, rich tobacco, floral, fruity, green and earthy aroma and taste nuances both prior to and on smoking in smoking tobacco and smoking tobacco article components.

Examples of the cyclohexenyl-alpha-alkyl acrolein derivatives of our invention and their organoleptic properties are as follows:

TABLE I

| Structure of Compound | Flavor Characteristics | Fragrance Characteristics |
|---|---|---|
| Mixture of Compounds having the structures: | A powerful, spicy, cinnamon aroma and taste. | A green, cumin-like, spicy, cinnamon aroma. |
| with a predominant amount of the compound having the structure: prepared according to Example IV, infra. | | |
| A mixture of compounds defined according to the structures: and with a predominant amount of the compound having the structure: produced according to Example I(B), (distillation Fractions 5–10). | A cinnamon, cumin-like aroma and taste. | A cinnamon, cumin-like, floral (lily/lilac), ionone-like, orris-like aroma profile with burnt orris nuances. |
| A mixture of the compound defined according to the structure: produced according to Example I(B). | | A natural, orris, floral (violet), animalic and musky aroma. |
| A mixture of compounds having the structures: and with a predominant amount of the compound having the structure: | A spicy and cinnamon aroma profile. | A spicy and cinnamon aroma profile. |

TABLE I-continued

| Structure of Compound | Flavor Characteristics | Fragrance Characteristics |
|---|---|---|
| 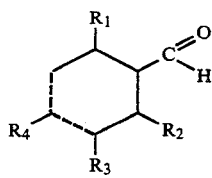 produced according to Example II. A mixture of compounds having the structures: 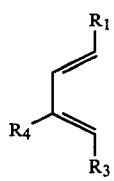 and 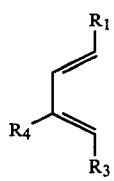 with a predominant amount of the compound having the structure: 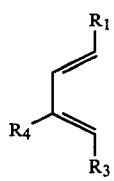 produced according to Example III. | A leafy, green, dandeloin leaf-like aroma and taste profile. | A pungent, fresh green, woody, "tropical rain forest" aroma. |

The cyclohexenyl-alpha-alkyl acrolein derivatives of our invention can be prepared according to one of two techniques. The first technique involve first providing a methyl-substituted cyclohexene carboxaldehyde having the structure:

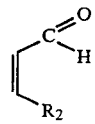

for example, by means of:

(a) Diels-Alder reaction of a conjugated diene having the structure:

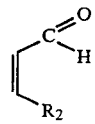

with an acrolein derivative having the structure:

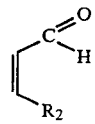

according to the reaction:

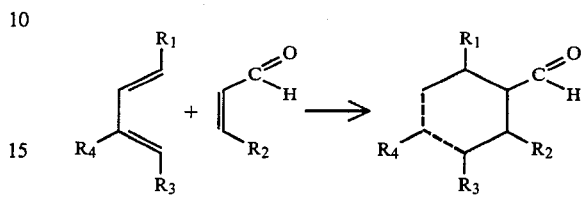

and then reacting the cyclohexene carboxaldehyde having the structure:

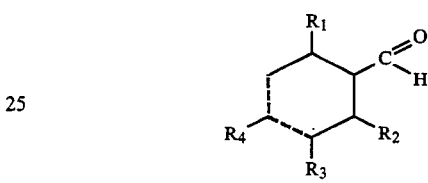

with propionaldehyde or butyraldehyde defined according to the structure:

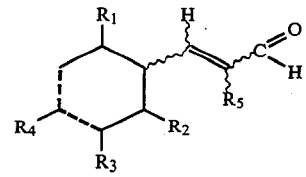

wherein $R_1$, $R_2$, $R_3$ and $R_4$ represent hydrogen or methyl with the proviso that one, two or three of $R_1$, $R_2$, $R_3$ and $R_4$ represent methyl; wherein $R_5$ represents methyl or ethyl; wherein one of the dashed lines represents a carbon-carbon double bond and the other of the dashed lines represents a carbon-carbon single bond; wherein the wavy lines represent the "cis" or "trans" juxtaposition of the moieties hydrogen, $R_5$, cyclohexenyl and carboxaldehyde about the carbon-carbon double bond; or (b) Carrying out a Vilsmeier Formulation according to the procedure taught in Chem. Communications, October 1979, pages 799-801 (article by Dauphin, "Vilsmeier Formulation of Limonene. The new method for synthesis of alpha-Atlantone"), according to the reactions:

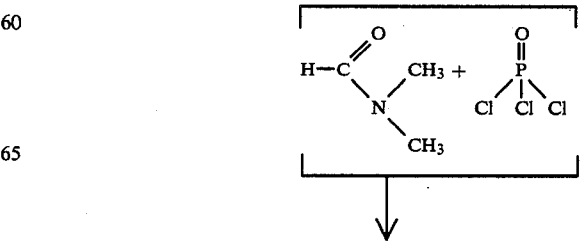

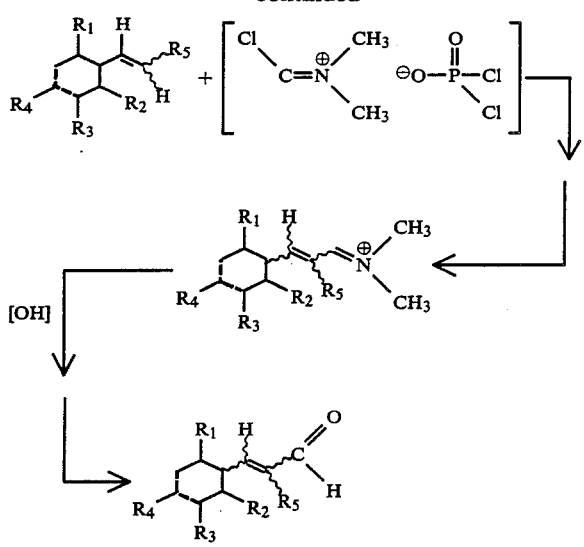

wherein $R_1$, $R_2$, $R_3$ and $R_4$ represent hydrogen or methyl with the proviso that one, two or three of $R_1$, $R_2$, $R_3$ and $R_4$ represent methyl; wherein $R_5$ represents methyl or ethyl; wherein one of the dashed lines represents a carbon-carbon double bond and the other of the dashed lines represents a carbon-carbon single bond; wherein the wavy lines represent the "cis" or "trans" juxtaposition of the moieties hydrogen, $R_5$, cyclohexenyl and carboxaldehyde about the carbon-carbon double bond.

In the first reaction sequence, the Diels-Alder reaction:

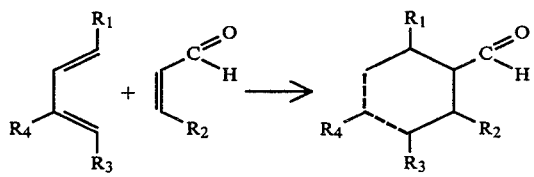

is carried out in accordance with the procedure of French Pat. No. 672,025 published on Dec. 21, 1929, the disclosure for which is incorporated by reference herein. In addition, the Diels-Alder reaction can be carried out at lower temperatures using Lewis acid catalyst such as stannic chloride, zinc chloride, aluminum diethyl chloride or ethyl aluminum dichloride (e.g., temperatures of 10°–40° C.). The resultant cyclohexene carboxaldehyde defined according to the structure:

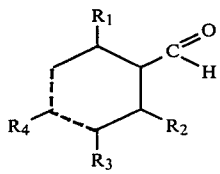

is then reacted via an aldol condensation reaction with n-propanal or n-butanal having the structure:

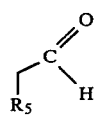

according to the reaction:

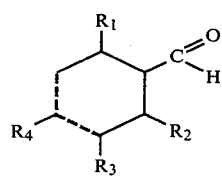

wherein $R_1$, $R_2$, $R_3$ and $R_4$ represent hydrogen or methyl with the proviso that one, two or three of $R_1$, $R_2$, $R_3$ and $R_4$ represent methyl; wherein $R_5$ represents methyl or ethyl; wherein one of the dashed lines represents a carbon-carbon double bond and the other of the dashed lines represents a carbon-carbon single bond; wherein the wavy lines represent the "cis" or "trans" juxtaposition of the moieties hydrogen, $R_5$, cyclohexenyl and carboxaldehyde about the carbon-carbon double bond.

The aldol condensation is carried out at standard aldol condensation reaction conditions using a base such as sodium hydroxide, potassium hydroxide, calcium hydroxide, lithium hydroxide or barium hydroxide (in, for example, a Soxhlet apparatus) at temperatures in the range of from about 10° C. up to about 80° C. in the presence of an inert compatibles such as methyl alcohol or ethyl alcohol. When using a barium hydroxide catalyst, the barium hydroxide is kept in the Soxhlet thimble and the reactants are refluxed at the reflux temperature of the reaction mass. The reaction can be carried out at atmospheric or super atmospheric pressures. At super atmospheric pressures the time for reaction completion is less than the time for reaction completion when carrying out the reaction at atmosphereic pressure in view of the higher temperature of reaction. The mole ratio of aldehyde having the structure:

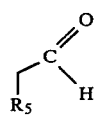

to aldehyde having the structure:

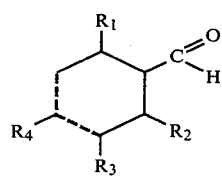

is preferably from about 0.5:1 up to about 1:0.5 with a mole ratio of 1:1 being preferred.

At the end of the reaction, the reaction mass is neutralized and the solvent is stripped. The reaction product is then distilled as by fractional distillation in vacuo to yield the desired products defined according to the structure:

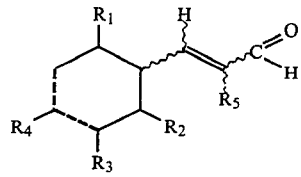

wherein $R_1$, $R_2$, $R_3$ and $R_4$ represent hydrogen or methyl with the proviso that one, two or three of $R_1$, $R_2$, $R_3$ and $R_4$ represent methyl; wherein $R_5$ represents methyl or ethyl; wherein one of the dashed lines represents a carbon-carbon double bond and the other of the dashed lines represents a carbon-carbon single bond; wherein the wavy lines represent the "cis" or "trans" juxtaposition of the moieties hydrogen, $R_5$, cyclohexenyl and carboxaldehyde about the carbon-carbon double bond.

The conditions for the Vilsmeier Formulation are the same as those set forth in the Dauphin paper, the disclosure of which is incorporated by reference herein.

The resultant product is a mixture of "cis" and "trans" isomers, to wit:

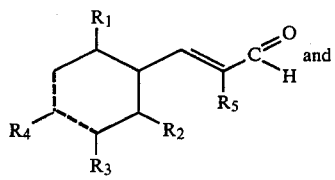

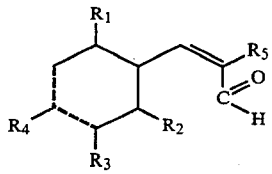

and, in addition, is a mixture of "endo" and "exo" isomers, for example:

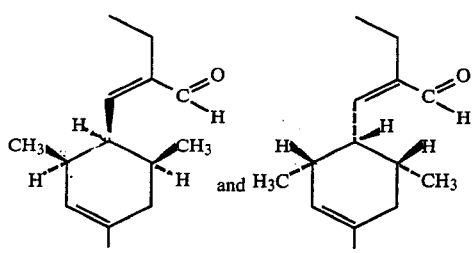

which represents, respectively, "cis" or "E" exo, exo, exo or endo, endo, endo. The different products can be trapped out using commercial GLC separations, but more practically they can be used in admixture for their collective organoleptic properties as set forth, infra and supra. Both the Vilsmeier Formulation and the foregoing Aldol condensation techniques however, yield products which are primarily "E" isomers, those which are defined according to the structure:

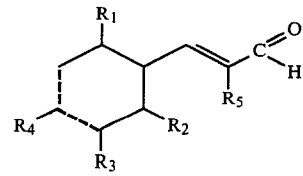

in preponderance over the "Z" isomers.

It is noteworthy that the compounds of our invention have several asymmetric carbon atoms which give rise to a vast number of "endo" and "exo" isomers in addition to the "cis" and "trans" isomers. Thusly, the "*" is indicative of the location of the asymmetric carbon atoms in the following structure:

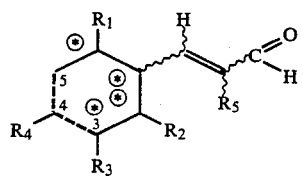

wherein $R_1$, $R_2$, $R_3$ and $R_4$ represent hydrogen or methyl with the proviso that one, two or three of $R_1$, $R_2$, $R_3$ and $R_4$ represent methyl; wherein $R_5$ represents methyl or ethyl; wherein one of the dashed lines represents a carbon-carbon double bond and the other of the dashed lines represents a carbon-carbon single bond; wherein the wavy lines represent the "cis" or "trans" juxtaposition of the moieties hydrogen, $R_5$, cyclohexenyl and carboxaldehyde about the carbon-carbon double bond.

When the cyclohexnyl-alpha-alkyl acrolein derivatives of our invention are used as food flavor adjuvants, the nature of the co-ingredients included with said cyclohexenyl-alpha-alkyl acrolein derivatives of our invention in formulating the product composition will also serve to alter, modify, augment or enhance the organoleptic characteristics of the ultimate foodstuff treated therewith.

As used herein in regard to flavors, the terms "alter", "modify" and "augment" in their various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible material which usually do, but need not, have nutritional value. Thus, foodstuffs include soups, convenience foods, beverages, dairy products, candies, vegetables, cereals, soft drinks, snacks, and the like.

As used herein, the term "medicinal product" includes both solids and liquids which are ingestible, non-toxic materials which have medicinal value such as cough syrups, cough drops, aspirin and chewable medicinal tablets.

The term "chewing gum" is intended to mean a composition which comprises a substantially water insoluble, chewable plastic gum base such as chicle, or substitutes therefor, including jelutong, guttakay, rubber or certain comestible natural or synthetic resins or waxes. Incorporated with the gum base in admixture therwith may be plasticizers or softening agents, e.g., glycerine, and a flavoring composition which incorporates one or more of the cyclohexenyl-alpha-alkyl acrolein derivatives of our invention, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterised as flavoring adjuvants or vehicles comprising, broadly, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxy anisole), butylated hydroxytoluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates; starches, pectins, and emulsifiers, e.g., mono- and diglycerides of fatty acids, skim milk powder, hexoses, pentoses, disaccharides, e.g., sucrose, corn syrup and the like.

Surface active agents include emulsifying atents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like, firming agents such as aluminum sodium sulfate, calcium chloride and calcium gluconate; texturizers, anticaking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexanoic acid benzoic acid, n-butyric acid, caproic acid, caprylic acid, cinnamic acid, isobutyric acid, isovaleric acid; alpha-methylbutyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanol, crotonal, diacetyl, 2-methylbutanal, beta,-beta-dimethyl acrolein, methyl n-amyl ketone, n-hexanal, 2-hexenal, isopentanal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, beta-damascone, alpha-damascone, beta-damascenone, acetophenone, 2-heptanone, o-hydroxy-acetopenone, 2-methyl-2-hepten-6-one, 2-octanone, 2-undecanone, 3-phenyl-4-pentenal, 2-phenyl-2-hexenal, 2-phenyl-2-pentenal, furfural, 5-methylfurfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpinhydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl carpylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alphamethylphenylglycidate, ethyl succinate, isobutyl cinnamate, cinnamyl formate, methyl cinnamate, and terpnyl acetate; hydrocarbons such as dimethyl naphthalene, dodecane, methyldiphenyl, methyl naphthalene, myrcene, naphthalene, octadecane, tetradecane, tetramethylnaphthalene, tridecane, trimethylnaphthalene, undecane, caryophyllene, alpha-phellandrene, beta-phellandrene, p-cymene 1-alpha-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essentail oil, safran oil, Bulgarian rose, capsicum, yara and vanilla; lactones such as $\gamma$-nonalactone; sulfides, e.g., methyl sulfide and other materials such as maltol, and acetals (e.g., 1,1-diethoxyethane, 1,1-dimethoxyethane and dimethoxymethane), piperine, chavicine, and piperidine.

The specific flavoring adjuvant selected for use may be either solid or liquid depending upon the desired physical form of the ultimate product, i.e., foodstuff, whether simulated or natural, and should, in any event, (i) be organoleptically compatable with the oxabicyclooctane derivatives and the cyclohexenyl-alpha-alkyl acrolein derivatives of our invention by not covering or spoiling the organoleptic properties (aroma and/or taste) thereof; (ii) be non-reactive with the cyclohexenyl-alpha-alkyl acrolein derivatives of our invention; and (iii) be capable of providing an environment in which the cyclohexenyl-alpha-alkyl acrolein derivatives of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product to toothpaste to which the flavor and/or aroma are to be imparted, modified, altered or enhanced. In contradistinction, in the preparation of solid products, e.g., simulated foodstuffs, ingredients capable of providing normally solid compositions should be selected wuch as various cellulose derivatives.

As will be appreciated by those skilled in the art, the amount of cyclohexenyl-alpha-alkyl acrolein derivatives of our invention employed in a particular instance can vary over a relatively wide range, depending upon the desired organoleptic effects to be achieved. Thus, correspondingly, greater amounts would be necessary in those instances wherein the ultimate food composition to be flavored (e.g., with a spice flavor or a specific black pepper-like-flavor) is relatively bland to the taste whereas relatively minor quantities may suffice for purposes of enhancing the composition merely deficient in natural flavor or aroma.

The primary requirement is that the amount selected be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of cyclohexenyl-alpha-alkyl acrolein derivatives of our invention will, of course, substantially vitiate any possibility of obtaining the desired results while excess quantities prove needlessly costly and in extreme cases may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of cyclohexenyl-alpha-alkyl acrolein derivatives of our invention ranging from a small but effective amount, e.g., 0.02 parts per million up to about 500 parts per million based on total composition, are suitable. Concentrations in excess of the maximum quantity stated are not normally recommended since they fail to provide commensurate enhancement of organoleptic properties. In those instances wherein the cyclohexenyl-alpha-alkyl acrolein derivatives of our invention are added to the foodstuff as an integral component of a flavoring composition, it is, of course, essential that the total quantity of flavoring composition employed be sufficient to yield an effective cyclohexenyl-alpha-alkyl acrolein derivatives of our invention concentration in the foodstuff product.

Food flavoring compositions prepared in accordance with the present invention preferably contain the cyclohexenyl-alpha-alkyl acrolein derivatives of our invention in concentrations ranging from about 0.0025% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the cyclohexenyl-alpha-alkyl acrolein derivatives of our invention with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix, are obtained by mixing the dried solid components, e.g., starch, sugar and the like, and the cyclohexenyl-alpha-alkyl acrolein derivatives of our invention in a dry blender until the requisite degree of uniformity is achieved.

It is presently preferred to combine with the cyclohexenyl-alpha-alkyl acrolein derivatives of our invention, the following adjuvants: Oil of Cubeb; Phellandrene; $\beta$-Phellandrene; Oil of Coriander; Oil of Pimento Leaf, Oil of Patchouli; Natural Lemon Oil; Acetaldehyde; $\alpha$-Terpineol; Citral; Carvone; Terpinolene; $\alpha$-Terpinene; Diphenyl; $\alpha$-Fenchyl Alcohol; Cineole; Limonene; Lindalool; Geranyl Acetate; Nootkatone; Neryl Acetate; Heliotropin; Maltol, Vanillin; Ethyl Maltol; Ethyl Vanillin; Anisaldehyde; Alpha Pinene; Beta-Pinene; Beta-Caryophyllene; Dihydrocarveol; Piperonal; Piperine; Chavicine; Piperidine; Oil of Black Pepper; Black Pepper Oleorsin; Capsicum; Oil of Nutmeg; Cardamon Oil; Clove Oil; Separmint Oil; Oil of Peppermint; and $C_{10}$-Terpinyl Ethers as described in application for U.S. patent, Ser. No. 872,937 filed on Jan. 27, 1978, now U.S. Pat. No. 4,131,687 issued on Dec. 26, 1978 (such as fenchyl ethyl ethers), 3-phenyl-3-pentenal dimethyl acetal, cinnamaldehyde, nutmeg oil, dibenzyl ether, eugenol, ethyl vanillin, oil of bitter almond, oil of cinnamon bark, oil of cloves, oil of cardamon, oil of nutmeg, oil of lemon, 2-phenyl-4-pentenal dimethyl acetal, 2-(2'-n-butyl)-4,5-dimethyl thiazoline.

The cyclohexenyl-alpha-alkyl acrolein derivatives of our invention can be used to contribute green, cuminlike, spicy, cinnamon, orris, floral, animalic, musky, lily, lilac, ionone-like, burnt orris, bungent, fresh, green, woody, "tropical rain forest" aroma nuances to perfumes, perfumed articles and colognes. As olfactory agents, the cyclohexenyl-alpha-alkyl acrolein derivatives of our invention can be formulated into or used as components of a "perfume composition" or can be used as components of a "perfumed article" or the perfume composition may be added to perfumed articles.

The term "perfume composition" is used herein to mean a mixture of organic compounds including, for example, alcohols, aldehydes, other than the aldehydes of the instant invention, ketones, nitriles, ethers, lactones, natural essential oils, synthetic essential oils and frequently hydrocarbons which are admixed so that the combined odors of the individual components produce a pleasant or desired fragrance. Such perfume compositions usually contain; (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling, fresh-smelling materials.

In perfume compositions, the individual component will contribute its particular olfactory characteristics, but the overall effect of the perfume composition will be the sum of the effects of each of the ingredients. Thus, the individual compounds of our invention, or mixtures thereof, can be used to alter the aroma characteristics of a perfume composition, for example, by highlighting or moderating the olfactory reaction contributed by another ingredient in the composition.

The amount of the cyclohexenyl-alpha-alkyl acrolein derivatives of our invention which will be effective in perfume compositions depends on many factors, including the other ingredients, their amounts and the effects which are desired. It has been found that perfume compositions containing as little as 0.05% of the cyclohexenyl-alpha-alkyl acrolein derivatives of our invention, or even less, can be used to impart an interesting green, cumin-like, spicy, cinnamon, orris, violet-flower-like, animalic, musky, lily, lilac, ionone-like, burnt orris, pungent, fresh, green, woody and "tropical rain forest" aromas to soaps, liquid and solid cationic, anionic, non-ionic or zwitterionic detergents, cosmetics, powders, liquid and solid fabric softeners, perfumed polymers per se such as polyethylene and polypropylene, optical brightener compositions and other products. The amount employed can range up to 50% or higher and will depend on considerations of cost, nature of the end product, and the effect desired on the finished product and particular fragrance sought.

The cyclohexenyl-alpha-alkyl acrolein derivatives of our invention can be used alone or in a perfume composition as an olfactory component in detergents and soaps, space odorants and deodorants; perfumes; colognes, toilet waters; bath salts; hair preparations such as lacquers, brilliantines, pomades, and shampoos; cosmetic preparations such as creams, deodorants, hand lotions, and sun screens; powders such as talcs, dusting powders, face powder, and the like. When used as an olfactory component of a perfumed article, as little as 0.01% of one or more of the cyclohexenyl-alpha-alkyl acrolein derivatives of our invention will suffice to impart an interesting green, cumin-like, spicy, cinnamon, orris, violet flower, animalic, musky, lily, lilac, ionone-like, burnt orris, bungent, fresh, green, woody, and/or "tropical rain forest" aromas. Generally, no more than 0.5% is required in the perfumed article. Accordingly, the perfumed articles of our invention can contain from about 0.01% up to about 0.5% by weight of the perfumed article of the cyclohexenyl-alpha-alkyl acrolein derivatives of one or more of our invention.

In addition, the perfume composition of our invention can contain a vehicle or carrier for the cyclohexenyl-alpha-alkyl acrolein derivatives of our invention alone or with other ingredients. The vehicle can be a liquid such as an alcohol such as ethanol, a glycol such as propylene glycol, or the like. The carrier can be an absorbent solid such as a gum (e.g., guar gum or xanthan gum or gum arabic) or components for encapsulating the composition such as gelatin (as by coacervation) or a urea formaldehyde prepolymer (to form a urea formaldehyde polymer wall around the liquid perfume center) which can be used to form a capsule wall surrounding the perfume oil.

An additional aspect of our invention provides an organoleptically improved smoking tobacco product and additives therefor including methods of making the same which overcome problems heretofore encountered in the creation or enhancement of specific desired natural tobacco-like notes, particularly hay-clover-like, sweet, rich tobacco, floral, fruity, green, and earthy notes. Such notes, both prior to and on smoking, in both the main stream and the side stream, may now be readily be controlled and maintained at the desired uniform level regardless of variations in the tobacco components of the blend; or the nature of the filter used in conjunction with the smoking tobacco article.

This invention further provides improved tobacco additives and additives for materials used in the fabrication of tobacco articles (particularly smoking tobacco articles) and methods whereby desirable hay-clover-like, sweet, rich tobacco, floral, fruity, green and earthy notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient, one or more of the cyclohexenyl-alpha-alkyl acrolein derivatives of our invention.

In addition to the cyclohexenyl-alpha-alkyl acrolein derivatives of our invention, other flavoring and aroma additives may be added to the smoking tobacco material or substituted therefor either separately or in admixture with one or more of the cyclohexenyl-alpha-alkyl acrolein derivatives of our invention:

I. Synthetic Materials

Beta-methylcinnamaldehyde;
Eugenol;
Dipentene;
beta-Damascenone;
alpha-Damascenone;
alpha-Damascone;
beta-Damascone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexen-1-ol;
2-Methyl-5-isopropyl-1,3-nonadiene-8-one;
2-Methyl-5-isopropylacetophenone;
2-Hydroxy-2,5,5,8a-tetramethyl-1-)2-hydroxyethyl)-decahydronaphthalene;
Dodecahydro-3a,6,6,9a-tetramethylnaphtho(2,1-β)furan;
4-Hydroxyhexenoic acid, gamma-lactone;
Polyisoprenoid hydrocarbons defined in Example V of U.S. Pat. No. 3,589,372 issued on June 29, 1971.

II. Natural Oils

Celery seed oil;
Coffee extract;
Bergamot oil;
Cocoa extract;
Nutmeg oil;

Origanum oil.

An aroma and flavoring concentrate containing one or more of the cyclohexenyl-alpha-alkyl acrolein derivatives of our invention and, if desired, one or more of the above-indicated additional flavoring additives may be added to the smoking tobacco material, to the filter or to the leaf or paper wrapper or to a filter which is part of the smoking article. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste, but insofar as enhancement or the imparting of hay-clover, sweet, rich tobacco, floral, fruity, green and/or earthy notes prior to and on smoking in both the main stream and the side stream, we have found that satisfactory results are obtained if the proportion by weight of the sum total of cyclohexenyl-alpha-alkyl acrolein derivatives of our invention to smoking tobacco material is between 50 ppm and 1500 ppm (0.005%–0.15%) of the active ingredients to the smoking tobacco material. We have further found that satisfactory results are obtained if the proportions by weight of the sum total of cyclohexenyl-alpha-alkyl acrolein derivatives of our invention used to flavoring materials is between 0.05:1 and 0.50:1.

Any convenient method for incorporating the cyclohexenyl-alpha-alkyl acrolein derivatives of our invention may be employed. Thus, the cyclohexenyl-alpha-alkyl acrolein derivatives of our invention, taken alone or along with other flavoring additives may be dissolved in a suitable solvent such as foodgrade ethanol, pentane, diethyl ether and/or other volatile organic solvents, and the resulting solution may either be sprayed on the cured, cased and blended tobacco material; or the tobacco material or filter may be dipped into such solution. Under certain circumstances, a solution of one or more of the cyclohexenyl-alpha-alkyl acrolein derivatives of our invention taken alone or taken further together with other flavoring additives as set forth above, may be applied by means of a suitable applicator such as a brush or roller on the paper or leaf wrapper for the smoking tobacco product, or it may be applied to the filter by either spraying or dipping or coating.

Furthermore, it will be apparent that only a portion of the tobacco or substitute therefor need be treaded, and the thus-treated tobacco may be blended with other tobaccos before the ultimate tobacco product is formed. In such cases, the tobacco treated may have one or more of the cyclohexenyl-alpha-alkyl acrolein derivative of our invention in excess of the amounts or concentrations above indicated so that when blended with other tobaccos, the final product will have the percentage within the indicated range.

While our invention is particularly useful in the manufacture of smoking tobacco such as cigarette tobacco, cigar tobacco and pipe tobacco, other tobacco products formed from sheeted tobacco dust or fines may also be used. As stated, supra, the cyclohexenyl-alpha-alkyl acrolein derivatives of our invention can be incorporated with materials such as filter tip materials, seam paste, packaging materials and the like which are used along with the tobacco to form a product adapted for smoking. Furthermore, the cyclohexenyl-alpha-alkyl acrolein derivatives of our invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of tobacco plant parts or substitute materials or both.

It will thus be apparent that the cyclohexenyl-alpha-alkyl acrolein derivatives of our invention can be utilized to alter, modify, augment or enhance sensory properties, particularly organoleptic properties, such as flavor(s) and/or fragrance(s) of a wide variety of consumable materials.

The following examples serve to illustrate our invention, and this invention is to be considered restricted thereto only as indicated in the appended claims.

All parts and percentages given herein are by weight unless otherwise specified.

EXAMPLE I

PREPARATION OF 2,4,6-CYCLOHEX-4-ENYL-1-(2-METHYL PROP-2-ENAL)

Reaction:

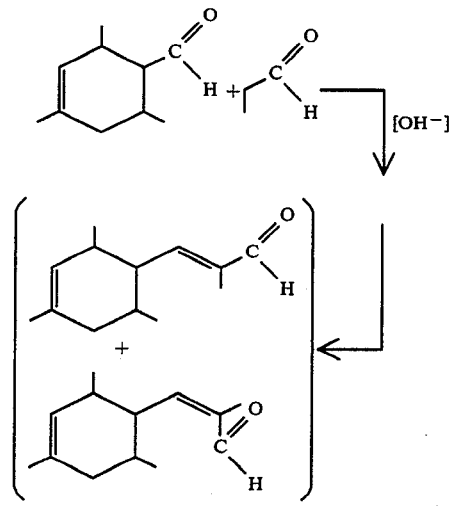

EXAMPLE I(A)

Into a 10-liter reaction vessel equipped with stirrer, thermometer, reflux condenser and heating coils are placed 3-liters of anhydrous methanol and 225 grams of potassium hydroxide. While maintaining the reaction mass at 25° C. and over a 15 minute period, 3495 grams of isocyclocitral having the structure:

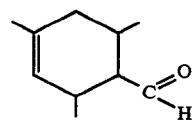

is charged to the reaction vessel. Over a period of 4 hours while maintaining the reaction mass at 20°–25° C., 1000 grams of propionaldehyde is charged to the reaction mass. The reaction mass is then stirred for a period of 30 minutes after which time 280 grams of acetic acid is added. The resulting product is then stripped of solvent and distilled on a 12"×1.5" Goodloe column yielding the following fractions:

| Fraction No. | Vapor Temp. (°C.) | Liquid Temp. (°C.) | Vacuum mm/Hg Pressure | Reflux Ratio | Wgt. of Fraction |
|---|---|---|---|---|---|
| 1 | /90 | /105 | 3.0 | 9:1 | 13.5 |
| 2 | 95 | 107 | 3.0 | 9:1 | 5.0 |
| 3 | 95 | 104 | 3.0 | 9:1 | — |
| 4 | 92 | 106 | 2.0 | 1:1 | 39.4 |
| 5 | 96 | 106 | 2.0 | 1:1 | 44.4 |
| 6 | 88 | 105 | 1.1 | 1:1 | 49.0 |
| 7 | 88 | 105 | 1.2 | 1:1 | 48.8 |
| 8 | 83 | 105 | 1.2 | — | 43.7 |
| 9 | 86 | 105 | 1.2 | 1:1 | 55.2 |
| 10 | 85 | 105 | 1.0 | 1:1 | 45.5 |
| 11 | 86 | 107 | 1.0 | 1:1 | 52.4 |
| 12 | 80 | 150 | 1.0 | 1:1 | 36.6 |

Figure 1:
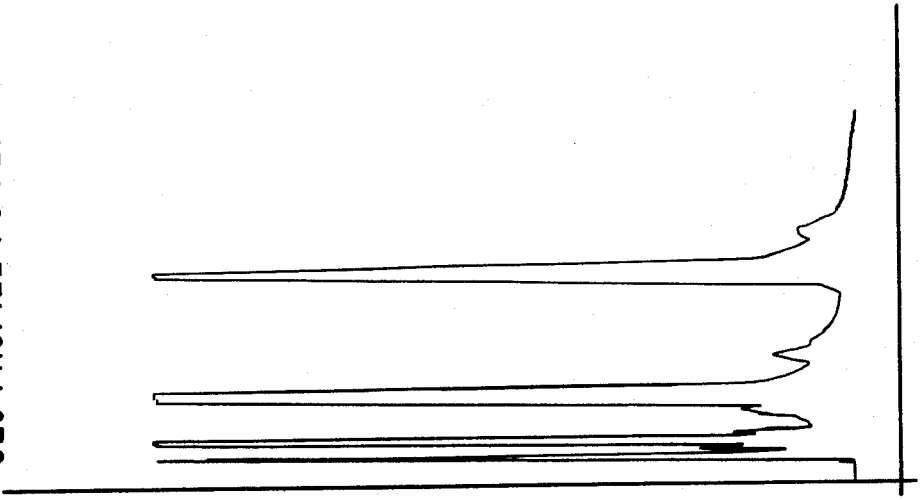
FIG. 1 is the GLC profile of the reaction product of Example I(A) containing the compounds having the structures.

FIG. 1 is the GLC profile of the reaction product prior to distillation.

The resulting reaction product is a mixture of compounds having the structures:

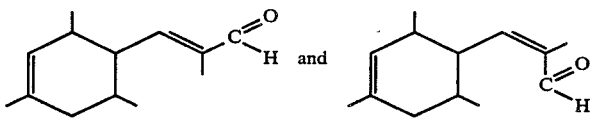

with a predominant amount (greater than 50%) of the compound having the structure:

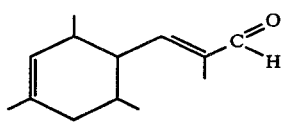

EXAMPLE I(B)

Into a 5-liter reaction vessel equipped with stirrer, thermometer, reflux condenser and heating coils is placed 50 grams of potassium hydroxide and 1-liter of anhydrous methyl alcohol. The reaction mass is cooled to 30° C. and while maintaining the reaction mass at 30° C., 900 grams of isocyclocitral having the structure:

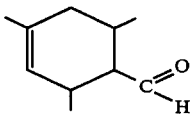

is charged to the reaction vessel. Over a period of 2 hours while maintaining the reaction mass at 30° C., 250 grams of propionaldehyde is charged to the reaction mass. The reaction mass is then stirred at 30° C. for a period of 30 minutes. At the end of the 30 minute period, 120 grams of acetic acid is added to the reaction mass. The reaction mass is then fractionally distilled at a vapor temperature of 83°-88° C. and a vacuum of 1.0-1.2 mm/Hg pressure to yield the product having the structure:

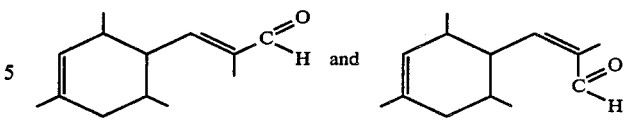

FIG. 2 is the GLC profile of the reaction product prior to distillation. The peak indicated by reference numeral "20" is the peak for the isocyclocitral reactant having the structure:

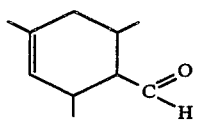

The peak indicated by reference numeral "21" is the peak for the product defined according to the structures:

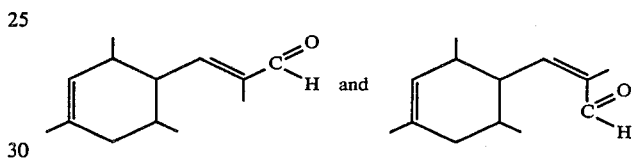

FIG. 2 is the NMR spectrum for the peak indicated by reference numeral "21" on FIG. 2 for the compound having the structures:

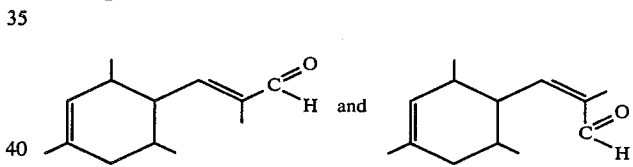

(solvent: CFCl$_3$; field strength 100 MH$_z$).

FIG. 4 is the infra-red spectrum for the compound indicated by the reference numeral "21" on FIG. 2 of the GLC profile having the structures:

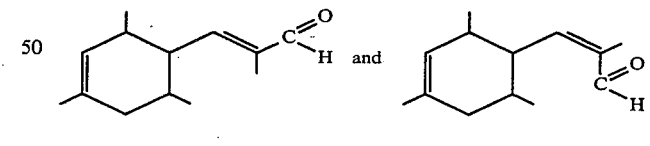

EXAMPLE II

PREPARATION OF ALPHA,2,4-TRIMETHYL-3-CYCLOHEXEN-1-ACROLEIN

Reaction:

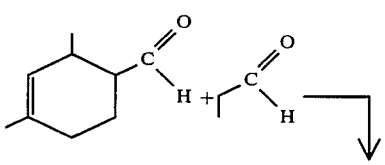

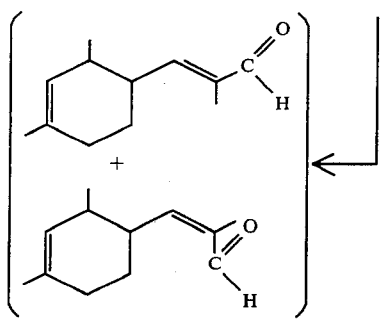

Into a 1-liter flask equipped with stirrer, thermometer, reflux condenser, addition funnel and cooling bath is placed 150 ml anhydrous methanol and 15 grams of potassium hydroxide. The reaction mass is cooled to room temperature and over a 1 hour period while maintaining the reaction temperature at 30° C. with cooling, a solution of 65 grams of propionaldehyde and 150 grams of the aldehyde having the structure:

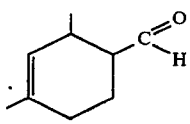

is added to the potassium hydroxide/methanol solution. The reaction mass is then stirred for a period of 2 hours whereupon GLC, NMR and IR spectra indicate that the reaction product having the structures:

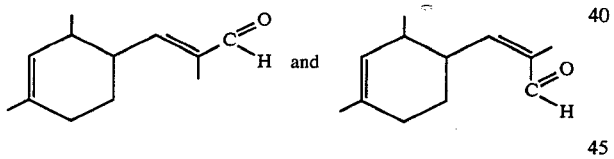

is formed.

FIG. 5 is the GLC profile for the crude reaction product prior to distillation (conditions: SE-30, column programmed at 200° C. isothermal). The reaction mass is distilled at 72° C. and 0.4 mm/Hg pressure, in 25 fractions. Bulked fractions 14 to 22 distilling at 70°–76° C. at 0.4 mm/Hg pressure has a spicy, cinnamic aroma and taste.

FIG. 6 is the NMR spectrum for Fraction 12 of this distillation containing the compounds having the structures:

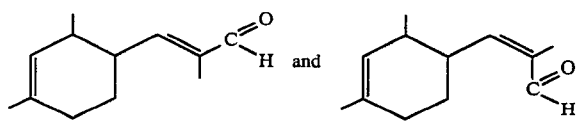

with a predominant amount of the compound having the structure:

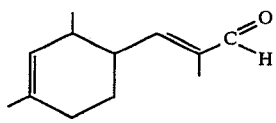

(solvent: CFCl$_3$; field strength 100 MH$_z$).

FIG. 7 is the infra-red spectrum for Fraction 12 of the foregoing distillation containing the compounds having the structures:

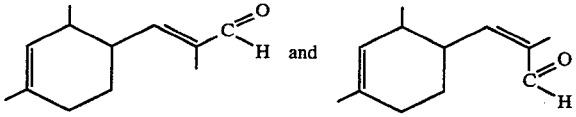

with a predominant amount of the compound having the structure:

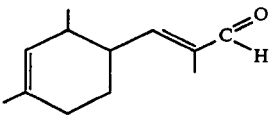

EXAMPLE III

PREPARATION OF ALPHA ETHYL-2,4,6-TRIMETHYL-3-CYCLOHEXEN-1-ACROLEIN

Reaction:

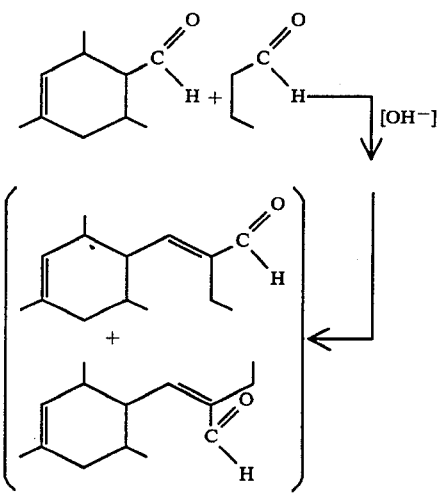

Into a 5-liter reaction flask equipped with stirrer, thermometer, reflux condenser, addition funnel and cooling bath is placed 50 grams of potassium hydroxide and 500 ml anhydrous methanol. The reaction product is cooled to room temperature (20°–23° C.) and over a period of 15 minutes, 1 kilogram (1000 grams) of isocyclocitral having the structure:

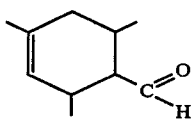

is added to the reaction mass. While maintaining the reaction temperature in the range of 30°-35° C., and over a period of 2 hours, 505 grams of n-butanal is added to the reaction mass. When the addition is complete, the reaction mass is stirred for a period of 2 hours. At the end of the 2 hour period, 1-liter of toluene and 1-liter of water is added to the reaction mass. The organic layer is separated from the aqueous layer, and if the organic layer is washed with water until the pH is between 6 and 7. The reaction mass is then distilled on a 4" splash column to yield the following fractions:

| Fraction No. | Vapor Temp. (° C.) | Liquid Temp. (° C.) | Vacuum mm/Hg. Pressure | Weight of Fraction |
| --- | --- | --- | --- | --- |
| 1 | /62 | /78 | 6.0 | 91.4 |
| 2 | 71 | 84 | 8.0 | 87.1 |
| 3 | 72 | 85 | 8.0 | 193.7 |
| 4 | 78 | 95 | 8.0 | 156.5 |
| 5 | 97 | 124 | 8.0 | 174.7 |
| 6 | 97 | 130 | 4.0 | 105.7 |
| 7 | 125 | 160 | 4.0 | 66.0 |
| 8 | 140 | 175 | 4.0 | 21.6 |

FIG. 8 is the GLC profile for the reaction product prior to distillation (SE-30 column programmed at 200° C. isothermal).

FIG. 9 is the NMR spectrum for the distilled reaction product containing the compounds having the structures:

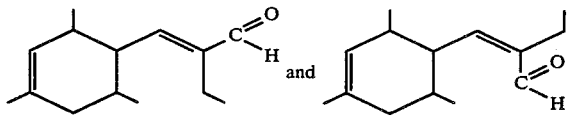

(solvent: CFCl₃; field strength 100 MHz).

FIG. 10 is the infra-red spectrum for the distillation product of the foregoing reaction product containing the compounds having the structures:

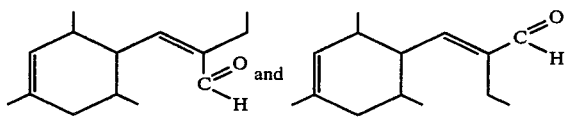

with the predominant amount of the compound having the structure:

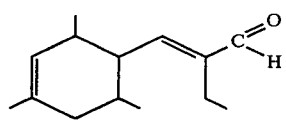

EXAMPLE IV

PREPARATION OF ALPHA,4-DIMETHYL-(4-CYCLOHEXENYL)ACROLEIN

Reaction:

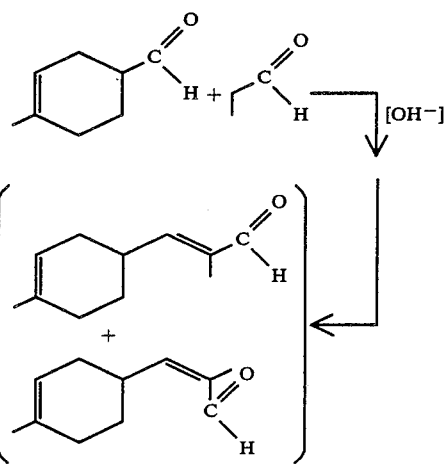

Into a 2-liter flask equipped with stirrer, thermometer, reflux condenser, addition funnel and heating mantle is place 40 grams of potassium hydroxide and 400 ml of anhydrous methanol. The resulting reaction mass is cooled to 30° C. and over a period of 2 hours while maintaining the reaction mass at 30° C. a mixture of the aldehyde having the structure:

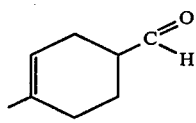

(400 grams) and 200 grams of propionaldehyde is added to the reaction mass. After adding the mixture of aldehyde having the structure:

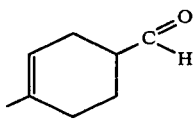

and propionaldehyde, the reaction mass is then stirred for a period of 2 hours at 30° C. At the end of the reaction, 2-liters of 10% aqueous sodium chloride and 1-liter of toluene is added to the reaction mass. The organic layer and the aqueous layer are separated and the organic layer is washed with water until the pH is between 6 and 7. The organic layer is then distilled on a 4" splash column to yield the following fractions:

| Fraction No. | Vapor Temp. (° C.) | Liquid Temp. (° C.) | Vacuum mm/Hg. Pressure | Weight of Fraction |
| --- | --- | --- | --- | --- |
| 2 | /83 | /105 | 2.0 | 96.5 |
| 2 | 93 | 115 | 1.5 | 91.4 |
| 3 | 108 | 148 | 1.6 | 100.4 |
| 4 | 156 | 184 | 1.8 | 90.5 |

-continued

| Fraction No. | Vapor Temp. (° C.) | Liquid Temp. (° C.) | Vacuum mm/Hg. Pressure | Weight of Fraction |
|---|---|---|---|---|
| 5 | 171 | 206 | 1.8 | 39.4 |

The resulting fractions 2–5 are bulked and redistilled on a 12"×1.5" Goodloe column to yield the following fractions:

| Fraction No. | Vapor Temp. (° C.) | Liquid Temp. (° C.) | Vacuum mm/Hg. Pressure | Weight of Fraction |
|---|---|---|---|---|
| 1 | 37/32 | 77/69 | 1.6/1.0 | 14.8 |
| 2 | 32 | 78 | 1.0 | 21.8 |
| 3 | 33 | 85 | 1.0 | 19.1 |
| 4 | 70 | 104 | 1.0 | 20.0 |
| 5 | 82 | 115 | 1.0 | 19.3 |
| 6 | 85 | 112 | 1.2 | 19.1 |
| 7 | 85 | 113 | 1.2 | 17.6 |
| 8 | 85 | 113 | 1.2 | 20.6 |
| 9 | 85 | 113 | 1.2 | 22.5 |
| 10 | 85 | 113 | 1.2 | 13.0 |
| 11 | 87 | 118 | 1.4 | 19.4 |
| 12 | 89 | 127 | 1.6 | 21.2 |
| 13 | 90 | 133 | 1.6 | 20.0 |
| 14 | 91 | 148 | 1.7 | 20.5 |
| 15 | 88 | 158 | 1.0 | 15.2 |
| 16 | 110 | 169 | 1.0 | 10.7 |
| 17 | 119 | 186 | 1.0 | 10.4 |
| 18 | 106 | 225 | 1.0 | 17.5 |

FIG. 11 is the GLC profile for the reaction product prior to distillation (SE-30, column programmed at 200° C. isothermal).

FIG. 12 is the NMR spectrum for Fraction 7 of the foregoing distillation containing the compounds having the structures:

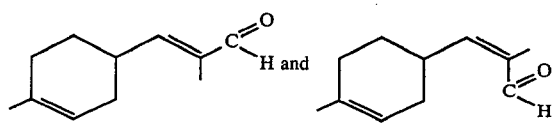

with the predominant amount of the compound having the structure:

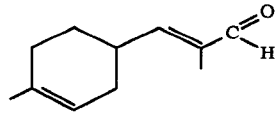

(solvent: CFCl$_3$; field strength 100 MH$_z$).

FIG. 13 is the infra-red spectrum for Fraction 7 of the foregoing distillation containing the compounds having the structures:

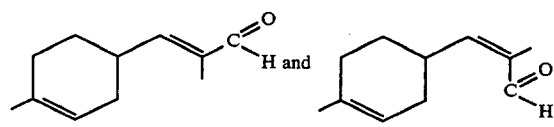

with a predominant amount of the compound having the structure:

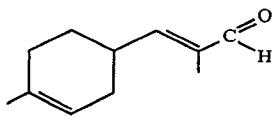

EXAMPLE V

NASTURTIUM FRAGRANCE

The following mixture is prepared:

| Ingredients | Parts by Weight |
|---|---|
| 3-Phenyl-4-pentenal dimethyl acetal | 8 |
| 3-Phenyl-3-pentenal dimethyl acetal | 10 |
| Ylang extra | 10 |
| Genaniol coeur | 50 |
| Citronellol coeur | 100 |
| Dimethyl benzyl carbinol | 15 |
| Phenyl ethyl alcohol coeur | 50 |
| Hexyl cinnamic aldehyde | 40 |
| 2-n-heptyl-cyclopentanone | 5 |
| Diels alder addition product of cyclopentadiene and 3-methyl-3-pentene-2-one having the structure: | 30 |
| Myrcenyl acetate | 1 |
| Geranonitrile | 20 |
| Geranyl acetate | 30 |
| Lavender | 20 |
| Nerole | 10 |
| Tetrahydro muguol | 60 |
| 4-(4-methyl,4-hydroxy amyl)Δ3-cyclohexane carboxaldehyde | 50 |
| Fraction 7 of the distillation product of the reaction product of Example IV containing the compounds having the structures: | 140 |

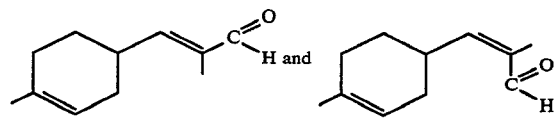

The compounds having the structures:

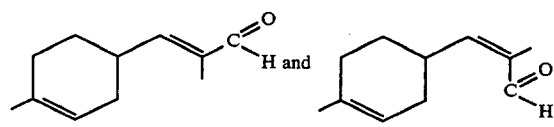

produced according to Example IV, Fraction 7 impart to this green, nasturtium fragrance a green, cumin, spicy, cinnamic aroma which is both powerful and long lasting. The entire aroma can be described as green, nasturtium with an intense cumin, spicy, cinnamic topnote.

EXAMPLE VI

GREEN, FLORAL FRAGRANCE

The following mixture is prepared:

| Ingredients | Parts by Weight |
|---|---|
| 3-Phenyl-4-pentenal ethylene acetal | 3.0 |
| 3-Phenyl-4-pentenal diisobutyl acetal | 4.0 |
| 2-oxa-1,1,3,3-tetramethyl-2,3,5,6,7,8-hexahydro-1H—benz(f)-indeae | 3.0 |
| Ylang extra | 5.0 |
| Geraniol coeur | 100.0 |
| Citronellol coeur | 70.0 |
| Dimethyl benzyl carbinol | 20.0 |
| Phenyl ethyl alcohol coeur | 30.0 |
| Hexyl cinnamic aldehyde | 30.0 |
| 2-n-heptyl-cyclopentanone | 2.0 |
| Diels Alder addition product of cyclopentadiene and 3-methyl-3-penten-2-one having the structure: | 20.0 |
| Linalyl acetate | 30.0 |
| n. Decanal | 2.0 |
| Geranonitrile | 30.0 |
| Orange terpenless | 10.0 |
| Geranyl acetate | 20.0 |
| Lavender | 10.0 |
| Nerole | 10.0 |
| 4-(4-methyl, 4-hydroxy amyl)Δ3-cyclohexene carboxaldehyde | 20.0 |
| Tetrahydro muguol | 40.0 |
| Mousse de Chene | 3.0 |
| Mixture of compounds having the structures: | 120.0 | and produced according to Example I(B), distillation Fractions 5–10

The use of the compounds having the structures:

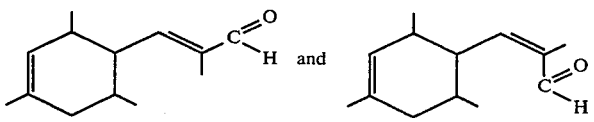 and imparts to this green, floral fragrance an intense and long lasting cinnamon, cumin-like, lily, lilac, ionone-like, orris-like, undertone and burnt orris topnote. Accordingly, the fragrance can be described as "green, floral with cinnamon, cumin-like, lily, lilac, ionone-like, orris undertone and a burnt orris topnote".

EXAMPLE VII

PREPARATION OF A COSMETIC POWDER COMPOSITION

A cosmetic powder is prepared by mixing in a ball mill 100 grams of talcum powder with 0.25 grams of the perfume substance set forth in Table II below. The resulting cosmetic powders have excellent aroma profiles as indicated in Table II below.

TABLE II

| Perfume Substance | Aroma Profile Imparted |
|---|---|
| Mixture of compounds having the stuctures: 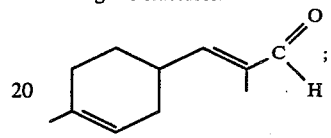 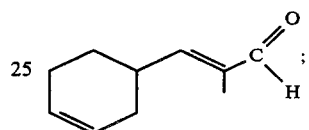 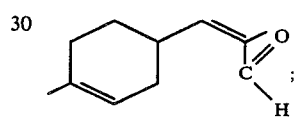 and 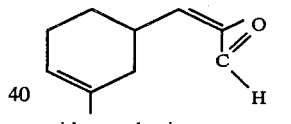 with a predominant amount of the compound having the structure: 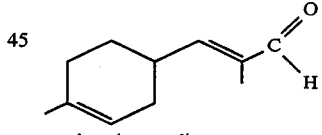 produced according to Example IV, infra. | A green, cumin-like, spicy, cinnamon aroma. |
| A mixture of compounds defined according to the structures: 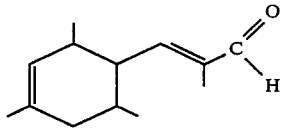 and 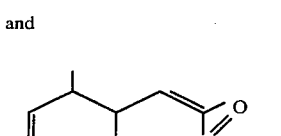 with a predominant amount of the compound having the structure: | A cinnamon, cumin-like, floral (lily/lilac), ionone-like, orris-like aroma profile with burnt orris nuances. |

TABLE II-continued

| Perfume Substance | Aroma Profile Imparted |
|---|---|
| 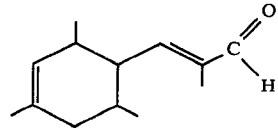 produced according to Example I(B), (distillation Fractions 5-10) | |
| A mixture of the compound defined according to the structure: 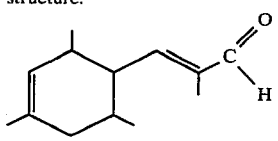 produced according to Example I(B) | A natural, orris, floral (violet), animalic and musky aroma. |
| A mixture of compounds having the structures: 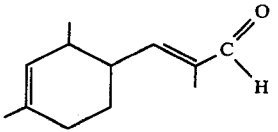 and 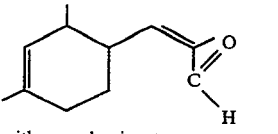 with a predominant amount of the compound having the structure: 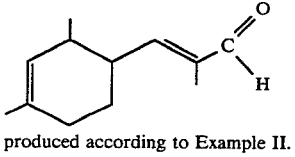 produced according to Example II. | A spicy and cinnamon aroma profile. |
| A mixture of compounds having the structures: 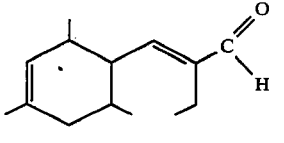 and 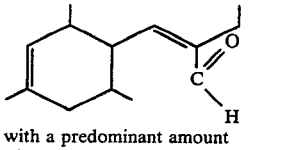 with a predominant amount of the compound having the structure: 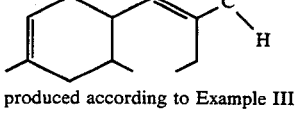 produced according to Example III. | A pungent, fresh green, woody, "tropical rain forest" aroma. |

TABLE II-continued

| Perfume Substance | Aroma Profile Imparted |
|---|---|
| Perfume composition of Example V. | A green, naturtium with an intense cumin, spicy, cinnamic topnote. |
| Perfume composition of Example VI. | A green, floral with cinnamon, cumin-like, lily, lilac, ionone-like, orris undertone and a burnt orris topnote. |

EXAMPLE VIII

PREPARATION OF SOAP COMPOSITION 100 grams of soap chips are mixed with 1 gram of each of the perfume materials of Table II of Example VII until a substantially homogeneous composition is obtained. The resulting mixture is melted and maintained at 10 atmospheres pressure at a temperature of 180° C. for a period of 4 hours. At the end of the 4 hour period, the resulting homogeneous mixture is cooled. The perfumed soap composition manifests manifests an excellent aroma character as set forth in Table II of Example VII.

EXAMPLE IX

PREPARATION OF A DETERGENT COMPOSITION

A granular detergent composition is prepared according to Example 9 of Canadian Pat. No. 1,004,566 (the disclosure of which is incorporated by reference herein) containing the following ingredients:

| Component | Weight % |
|---|---|
| Anhydrous sodium carbonate | 30.0 |
| Hydrated sodium silicate (81.5% solids, $SiO_2:Na_2O$ ratio-2.1:1 by weight) | 20.0 |
| Coconut alcohol condensed with 6 molar proportions of ethylene oxide | 10.0 |
| Sodium citrate dihydrate | 10.0 |
| Sodium dichlorocyanurate dihydrate | 3.8 |
| Polyethylene glycol (available under the trademark Carbowax 4000, M.W. 3000-3700) | 2.0 |
| Dimethyl silicone | 0.8 |
| Anhydrous sodium sulfate | 15.5 |
| Perfume substance as set forth in Table II of Example VII. | 5.9 |

The resulting detergent compositions have excellent aromas as set forth in Table II of Example VII.

EXAMPLE X

PREPARATION OF A DETERGENT COMPOSITION

A detergent is prepared from the following ingredients according to Example I of Canadian Pat. No. 1,007,948 (the disclosure of which is incorporated herein by reference):

| Ingredients | Parts by Weight |
|---|---|
| Neodol 45-11 (a $C_{14}$-$C_{15}$ alcohol ethoxylated with 11 moles of ethylene oxide) | 12 |
| Sodium carbonate | 55 |
| Sodium citrate | 20 |

-continued

| Ingredients | Parts by Weight |
| --- | --- |
| Sodium sulfate, water brighteners | q.s. |

This detergent is a phosphate-free detergent. A total of 100 grams of this detergent is admixed individually with 0.15 grams of each of the perfumery substances of Table II of Example VII, supra. Each of the detergents has excellent aromas as set forth in Table II of Example VII.

EXAMPLE XI

PERFUMED LIQUID DETERGENT

Concentrated liquid detergents with aroma nuances as set forth in Table II of Example VII containing a 0.10%, 0.15% and 0.20% of each of the perfumery substances of Table II of Example VII are prepared. They are prepared by adding and homogeneously admixing the appropriate quantity of each of the perfumery substances of Table II of Example VII in the liquid detergent. The degergents all possess excellent aromas as set forth in Table II of Example VII.

EXAMPLE XII

COLOGNE AND HANDKERCHIEF PERFUMES

The perfume substances of Table II of Example VII are each incorporated separately into colognes at concentrations of 1.5%, 2.0%, 2.5%, 3.0%, 4.0% and 5.0% in 70%, 75%, 80%, 85%, and 90% aqueous ethanol solutions; and into handkerchief perfumes at concentrations of 15%, 20%, 30% and 40% (in 80%, 85%, 90% and 95% aqueous ethanol solutions). Distinct and definitive strong fragrances are imparted to the colognes and to the handkerchief perfumes at the levels indicated according to the aroma profiles as set forth in Table II of Example VII.

EXAMPLE XIII

A tobacco blend is made up by mixing the following materials:

| Ingredient | Parts by Weight |
| --- | --- |
| Bright | 40.1 |
| Burley | 24.9 |
| Maryland | 1.1 |
| Turkish | 11.6 |
| Stem (flue cured) | 14.2 |
| Glycerin | 2.8 |
| Water | 5.3 |

The above tobacco is used in producing cigarettes, and the following formulation is compounded and incorporated into each of these cigarettes.

| Ingredients | Parts by Weight |
| --- | --- |
| Ethyl butyrate | 0.05 |
| Ethyl valerate | 0.05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model filter cigarettes are treated in the tobacco section with bulked fractions 5-10 of the reaction product of Example I(B) containing the compound having the structures:

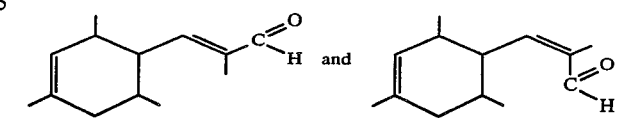

at 100 ppm per cigarette. Another one-third of these model cigarettes are treated in the filter with the mixture of compounds defined according to the structures:

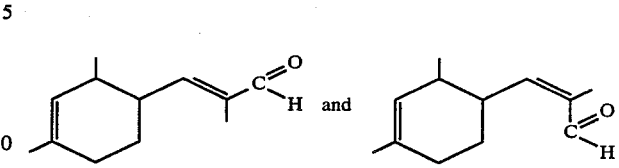

produced according to Example II. The last third of these cigarettes is left untreated. When evaluated by paired comparison, the cigarettes treated both in the tobacco and in the filter with the compounds of our invention are found in smoke flavor, to be more tobacco-like, with enhanced hay, clover-like, sweet, rich tobacco, floral, fruity, green and earthy aromas. The compounds having the structures:

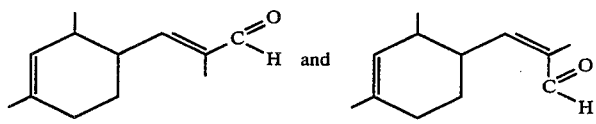

give rise to excellent, spicy, cinnamon nuances in addition to the hay-clover-like, floral, fruity, green and earthy aroma nuances in both the main stream and in the side stream on smoking.

EXAMPLE XIV

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent
   1 percent of the oxabicyclooctane derivative or cyclohexyl alkyl or alkenyl carbinol or ester thereof of our invention as set forth in the Table II of Example VII and giving rise to the aroma nuances as set forth in said Table II of Example VII.

Fabric-softening compositions prepared as set forth above having the above aroma characteristics essentially consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aromas as set forth in Table II of Example VII, supra above are imparted in a pleasant manner to the head space in the dryer on operation thereof using the said dryer added fabric softening nonwoven fabric.

EXAMPLE XV

The following mixture is prepared:

| Ingredients | Parts by Weight |
| --- | --- |
| 3-Phenyl-4-pentenal dimethyl acetal produced according to the procedure of Example I of U.S. Pat. No. 3,922,237 the specification for which is incorporated by reference herein | 3 |
| Cinnamic aldehyde | 8 |
| Orange oil | 3 |
| Oil of cloves | 1 |
| Phenyl ethyl alcohol | 5 |
| Mixture of compounds which are bulked distillation Fractions 5-10 produced according to Example I(B) containing the compounds having the structures: | 12 |

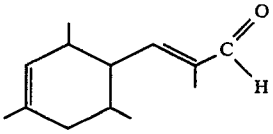

and

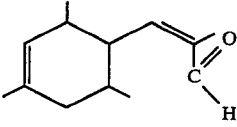

| | |
| --- | --- |
| Ethyl alcohol | 68 |

The addition of the mixture of compounds having the structures:

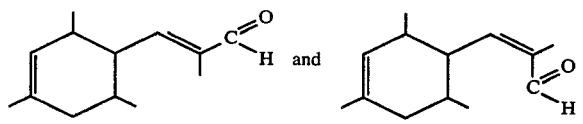

to this mixture imparts to the flavor a dominating, full-bodied cinnamon aroma. Without the mixture of compounds defined according to the structures:

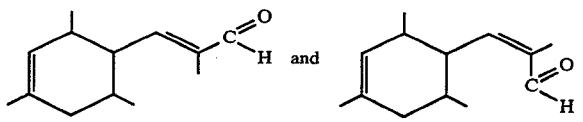

the flavor formulation is not as intense and requires approximately two times as much material when added to the standard cinnamon flavored powders for use in pastry powders and cake powders. The subject flavor formulation acts as an absolute replacement for cinnamon bark, Ceylon (*Cortex cinnamoni ceylanici*) when used as a flavor in baking. Thus, 420 grams of the above-mentioned flavor formulation are added to the following powder cake flavor oil which is then added at the rate of 0.25% to standard cake mix and appropriately baked:

| Mixture of Gm. | |
| --- | --- |
| 27.5 | ethyl vanillin |
| 126.0 | vanillin |
| 66.0 | oil of bitter almond |
| 420.0 | oil of cinnamon bark |
| 66.0 | oil of cloves |
| 33.0 | oil of cardamom |
| 66.0 | oil of nutmet |
| 195.5 | oil of lemon, cold pressed |
| Total 1000.0 | |

EXAMPLE XVI

A. Powder Flavor Composition

20 Grams of the flavor composition of Example XV is emulsified in a solution containing 300 grams of gum acacia and 700 grams of water. The emulsion is spray-dried with a Bowen Lab Model Dried utilizing 260 cfm of air with an inlet temperature of 500° F., an outlet temperature of 200° F. and a wheel speed of 50,000 rpm.

B. Sustained Release Flavor

The following mixture is prepared:

| Ingredients | Parts by Weight |
| --- | --- |
| Liquid cinnamon flavor containing one of the gamma methyl gamma cycloalkyl butyrolactones of Example XV | 20 |
| Propylene glycol | 9 |
| Cab-O-Sil ® M-5 (brand of silica produced by the Cabot Corporation, 125 High Street, Boston, Massachusetts 02110 | 5 |
| Physical properties: | |
| Surface Area: 200 m²/gm | |
| Nominal particle size: 0.012 microns | |
| Density: 2.3 lbs/cu.ft.) | |

The Cab-O-Sil ® is dispersed in the liquid cinnamon flavor composition of Example XV with vigorous stirring thereby resulting in a viscous liquid. 71 Parts by weight of the powder flavor composition of Part A, supra, is then blended into the said viscous liquid with stirring at 25° C. for a period of 30 minutes resulting in a dry, free-flowing, sustained release flavor powder.

EXAMPLE XVII

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example XV (containing one of the cyclohexenyl-alpha-alkyl acrolein derivatives of our invention produced according to Example I or Example II) is added to the solution which is then homogenized to form an emulsion having a particle size typically in the range of 5-40 microns. The material is kept at 120° F. under which conditions the gelatin will not gel.

Coacervation is induced by adding, slowly and uniformly, 40 parts by weight of 20% aqueous solution of sodium sulfate. During coacervation, the gelatin molecules are deposited uniformly about each oil droplet as a nucleus.

Gelation is effected by pouring the heated coacervate mixture into 1,000 parts by weight of 7% aqueous solution of sodium sulfate at 65° F. The resulting gelled coacervate may be filtered and washed with water at temperatures below the melting point of gelatin to remove the salt.

Hardening of the filtered cake in this example is effected by washing with 200 parts by weight of 30% solution of formaldehyde in water. The cake is then thoroughly washed with water to remove the residual formaldehyde.

EXAMPLE XVIII

CHEWING GUM

100 Parts by weight of chicle are mixed with 4 parts by weight of the flavor prepared in accordance with Example XV. 300 Parts sucrose and 100 parts corn syrup are added. Mixing is effected in a ribbon blender with jacketed side walls of the type manufactured by Baker Perkins Company.

The resultant chewing gum blend is then manufactured into strips 1" in width and 0.1" in thickness. The strips are cut into lengths of 3" each. On chewing, the chewing gum has a pleasant, long-lasting, cinnamon flavor.

EXAMPLE XIX

CHEWING GUM

100 Parts by weight of chicle are mixed with 18 parts by weight of the flavor prepared in accordance with Example XV, Part "B". 300 Parts of sucrose and 100 parts of corn syrup are then added. Mixing is effected in a ribbon blender with jacketed side walls of the type manufactured by the Baker Perkins Company.

The resultant chewing gum blend is then manufactured into strips 1" in width and 0.1" in thickness. The strips are cut into lengths of 3" each. On chewing, the chewing gum has a pleasant, very long-lasting, cinnamon flavor.

EXAMPLE XX

TOOTHPASTE FORMULATION

The following separate groups of ingredients are prepared:

| Parts by Weight | Ingredients |
|---|---|
| Group "A" | |
| 30.200 | Glycerine |
| 15.325 | Distilled water |
| .100 | Sodium benzoate |
| .125 | Saccharin sodium |
| .400 | Stannous fluoride |
| Group "B" | |
| 12.500 | Calcium carbonate |
| 37.200 | Discalcium phosphate (dihydrate) |
| Group "C" | |
| 2.000 | Sodium n-lauroyl sarcosinate |
| Group "D" | |
| 1.200 | Flavor material of Example XV, Part "B" |
| 100.000 (total) | |

Procedure

1. The ingredients in Group "A" are stirred and heated in a steam jacketed kettle to 160° F.
2. Stirring is continued for an additional 3 to 5 minutes to form a homogeneous gel.
3. The powders of Group "B" are added to the gel, while mixing, until a homogeneous paste is formed.
4. With stirring, the flavor of "D" is added and lastly, the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant cinnamon flavor of constant strong intensity throughout said procedure (1-1.5 minutes).

EXAMPLE XXI

CHEWABLE VITAMIN TABLETS

The flavor material produced according to the process of Example XV, Part "B", is added to a chewable vitamin tablet formulation at a rate of 10 grams per kilogram which chewable vitamin tablet formulation is prepared as follows:

In a Hobart Mixer, the following materials are blended to homogeneity:

| | Gms/1000 Tablets |
|---|---|
| Vitamin C (ascorbic acid) as ascorbic acid-sodium ascorbate mixture 1:1 | 70.11 |
| Vitamin B (thiamine mononitrate) as Rocoat ® thiamine mononitrate 33⅓% (Hoffman LaRoche) | 4.0 |
| Vitamin B (riboflavin) as Rocoat ® riboflavin 33⅓% | 5.0 |
| Vitamin B (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin B (cyanocobalamin as Merck 0.1% in gelatin | 3.5 |
| Vitamin E (di-alpha tocopheryl acetate) as dry Vitamin E acetate 33⅓% Roche | 6.6 |
| d-Biotin | 0.144 |
| Flavor of Example XV, Part "B" | (as indicated above) |
| Certified lake color | 5.0 |
| Sweetener - sodium saccharin | 1.0 |
| Magnesium stearate lubricant | 10.0 |
| Mannitol, q.a. to make | 500.00 |

Preliminary tablets are prepared by slugging with flat faced punches and grinding the slugs to 14 mesh. 13.5 Grams dry Vitamin A acetate and 0.6 grams Vitamin D are then added as beadlets. The entire blend is then compressed using concave punches at 0.5 grams each.

Chewing of the resultant tablets yields a pleasant, long-lasting consistently strong cinnamon flavor for a period of 12 minutes.

EXAMPLE XXIII

Scented polyethylene pellets having a pronounced aroma as set forth in Table II of Example VII, supra are prepared as follows:

Seventy-five pounds of polyethylene having a melting point of about 220° F. is heated to about 230° F. in a container of the kind illustrated in FIGS. 14 and 15.

Twenty-five pounds of one of the perfume compositions of Table II of Example VII is then quickly added to the liquified polyethylene, the lid 528 is put in place and the agitating means 573 are actuated. The temperature is maintained at about 225° F. and the mixing is continued for about 5–15 minutes. The valve "V" is then opened to allow flow of the molten polyethylene enriched with the perfume substance (one of the materials of Table II of Example VII) to exit through the orifices 534. The liquid falling through the orifices 534 solidifies almost instantaneously upon impact with the moving cooled conveyor 538. Polyethylene beads or pellets 544 having pronounced aromas as set forth in Table II of Example VII are thus formed. Analysis demonstrates that the pellets contain about 25% of the perfume substance of Table II of Example VII so that almost no losses in the scenting substance did occur. These pellets may be called "master pellets".

Fifty pounds of the scent containing "master pellets" are then added to one thousand pounds of unscented polyethylene powder and the mass is heated to the liquid state. The liquid is molded into thin sheets of films. The thin sheets of films have pronounced aromas as set forth in Table II of Example VII. The sheets of films are cut into strips ¼" in width×3" in length and placed into apparatus used for air fresheners. On operation of said apparatus as a room air freshener, after 4 minutes, the room has an aesthetically pleasing aroma as set forth in Table II of Example VII.

EXAMPLE XXIV

One hundred pounds of polypropylene are heated to about 300° F. Thirty pounds of one of the essences as described in Table II of Example VII, supra are added to the liquified polypropylene. The procedure is carried out in the apparatus shown in FIGS. 14 and 15. After mixing for about 8 minutes, the valve "V" is opened to allow the exit of the polypropylene scented material whereby solid pellets having pronounced aromas as set forth in Table II of Example VII are formed on the conveyor. The pellets thus obtained are then admixed with about twenty times their weight of unscented polypropylene and the mixture is heated and molded into "spaghetti" tows. The spaghetti tows are cut into small cylinders approximately 0.1" in length×0.02" in diameter. The cylinders have a strong and pleasant perfumed smell and scents as set forth in Table II of Example VII.

The cylinders are used in apparatus for air freshening and on operation of said apparatus, the environment surrounding the air freshener has a pleasant and faint aroma as set forth in Table II of Example VII.

EXAMPLE XXII

To a portion of essentially flavorless salad dressing, a 50:50 mole ratio mixture of 2-(2'-n-butyl)-4,5-dimethyl thiazoline and mixture of compounds defined according to the structures:

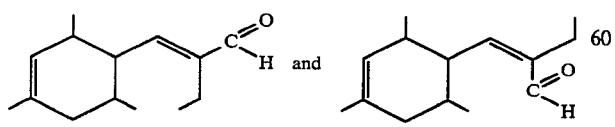

prepared according to Example III, supra is added at the rate of 0.10 ppm. The resulting mixture has a characteristic leafy, green, dandeloin leaf, cucumber, spiced pickle note. Without the 2-(2'-n-butyl)-4,5-dimethyl thiazoline the cucumber, spiced pickle note is missing but the excellent dandeloin leafy, green aroma and taste are present in a more intense fashion. The salad dressing is a mixture of the following:

| Ingredient | Parts by Weight |
|---|---|
| Black pepper oil | 3 |
| Nutmeg oil | 3 |
| Celery oil | 3 |
| Lemon oil | 3 |
| Mustard oil | 1 |
| Vinegar-citric acid (50:50 mixture) | 120 |
| Starch paste prepared from tapioca flour-water (50:50 mixture) | 300 |
| Liquid egg yolks | 210 |
| Sodium chloride | 7 |
| Sucrose | 10 |
| Mustard | 20 |
| Locust Bean gum | 6 |

What is claimed is:

1. A process for augmenting or enhancing the aroma of a consumable material selected from the group consisting of perfume compositions, colognes and perfumed polymers comprising the step of adding to said consumable material an aroma augmenting or enhancing quantity of at least one aldehyde having a structure selected from the group consisting of:

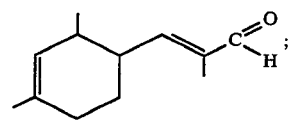

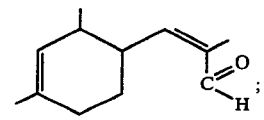

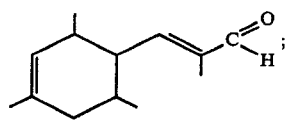

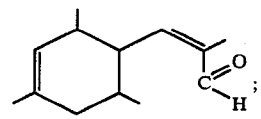

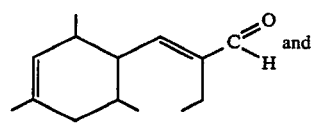

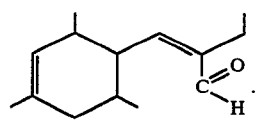

2. The process of claim 1 wherein the aldehyde has the structure:

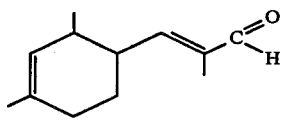

3. The process of claim 1 wherein the aldehyde has the structure:

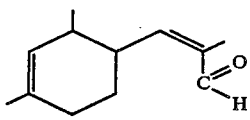

4. The process of claim 1 wherein the aldehyde has the structure:

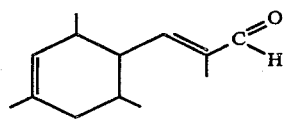

5. The process of claim 1 wherein the aldehyde has the structure:

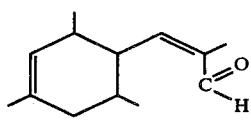

6. The process of claim 1 wherein the aldehyde has the structure:

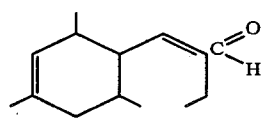

7. The process of claim 1 wherein the aldehyde has the structure:

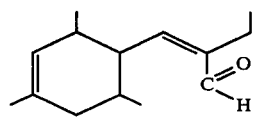

8. The process of claim 1 wherein the consumable material is a perfume composition or cologne.

9. The process of claim 1 wherein the consumable material is a perfumed polymer.

10. A process for augmenting or enhancing the aroma of a consumable material selected from the group consisting of perfume compositions, colognes and perfumed articles comprising the step of adding to said consumable material an aroma augmenting or enhancing quantity of a product containing a mixture of "cis" and "trans" isomers having the structures:

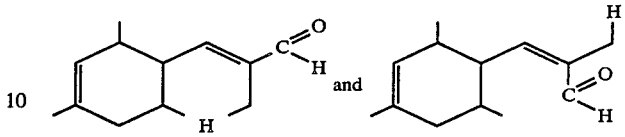

produced according to the process of reacting n-propanal with isocyclocitral having the structure:

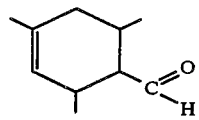

in the presence of an alkali metal hydroxide and methyl alcohol and then distilling the resulting product.

11. A process for augmenting or enhancing the aroma of a consumable material selected from the group consisting of perfume compositions, colognes and perfumed articles comprising the step of adding to said consumable material an aroma augmenting or enhancing quantity of a mixture of compounds having the structures:

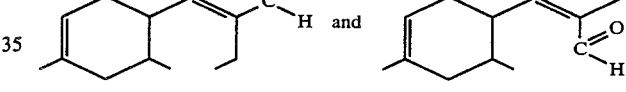

produced according to the process of reacting n-butanal with isocyclocitral having the structure:

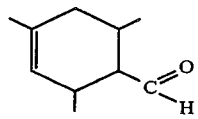

in the presence of an alkali metal hydroxide and methyl alcohol and then distilling the resulting product.

12. The process of claim 10 wherein the consumable material is a perfume composition, or a cologne.

13. The process of claim 10 wherein the consumable material is a perfumed article and the perfumed article is a perfumed polymer.

14. The process of claim 11 wherein the consumable material is a perfume composition, or a cologne.

15. The process of claim 11 wherein the consumable material is a perfumed article and the perfumed article is a perfumed polymer.

* * * * *